(12) United States Patent
Braun et al.

(10) Patent No.: US 10,470,671 B2
(45) Date of Patent: Nov. 12, 2019

(54) WEARABLE DEVICES FOR SENSING AND COMMUNICATING DATA ASSOCIATED WITH A USER

(71) Applicants: Zachary Joseph Braun, Atlanta, GA (US); Tyler Evan Sisk, Atlanta, GA (US)

(72) Inventors: Zachary Joseph Braun, Atlanta, GA (US); Tyler Evan Sisk, Atlanta, GA (US)

( * ) Notice: Subject to any disclaimer, the term of this patent is extended or adjusted under 35 U.S.C. 154(b) by 0 days.

(21) Appl. No.: 16/105,883

(22) Filed: Aug. 20, 2018

(65) Prior Publication Data

US 2019/0053719 A1 Feb. 21, 2019

Related U.S. Application Data

(63) Continuation of application No. 15/451,877, filed on Mar. 7, 2017, now Pat. No. 10,052,034.

(Continued)

(51) Int. Cl.
*H04Q 9/00* (2006.01)
*G08C 17/02* (2006.01)
*H04Q 9/14* (2006.01)
*A61B 5/0205* (2006.01)
*G06F 1/16* (2006.01)

(Continued)

(52) U.S. Cl.
CPC ........ *A61B 5/02055* (2013.01); *A61B 5/0008* (2013.01); *A61B 5/117* (2013.01); *A61B 5/6803* (2013.01); *A61B 5/6817* (2013.01); *G06F 1/163* (2013.01); *G06T 11/003* (2013.01); *A61B 5/021* (2013.01); *A61B 5/02405* (2013.01); *A61B 5/02438* (2013.01); *A61B 5/0816* (2013.01); *A61B 5/0833* (2013.01); *A61B 5/4866* (2013.01); *A61B 2503/20* (2013.01); *G02B 27/017* (2013.01); *G06T 11/206* (2013.01); *G06T 2200/24* (2013.01)

(58) Field of Classification Search
CPC .................................................. A61B 5/02055
See application file for complete search history.

(56) References Cited

U.S. PATENT DOCUMENTS

2004/0135693 A1* 7/2004 Schubert ............ G08B 21/0453
340/573.1
2010/0010832 A1* 1/2010 Boute ................. G06F 19/3418
705/3

(Continued)

*Primary Examiner* — Joseph H Feild
*Assistant Examiner* — Pameshanand Mahase
(74) *Attorney, Agent, or Firm* — Troutman Sanders LLP; Ryan A. Schneider; Micah B. Hensley

(57) ABSTRACT

Embodiments of the present disclosure can comprise a wearable device for sensing and communicating data associated with a condition of a user. In some embodiments, the wearable device can comprise a biometric sensor unit configured to sense biometric data associated with a physiological condition of the user, a display unit configured to display a visual representation of the sensed biometric data from the biometric sensor unit to the user and a control unit operatively coupled to the biometric sensor unit and the display unit. The control unit may also comprise at least one processor configured to receive indications of the sensed biometric data and a communication unit configured to transmit and/or receive information associated with the sensed biometric data.

20 Claims, 22 Drawing Sheets

Related U.S. Application Data

(60) Provisional application No. 62/304,728, filed on Mar. 7, 2016.

(51) Int. Cl.
*A61B 5/00* (2006.01)
*A61B 5/117* (2016.01)
*G06T 11/00* (2006.01)
G06T 11/20 (2006.01)
G02B 27/01 (2006.01)
A61B 5/024 (2006.01)
A61B 5/083 (2006.01)
A61B 5/08 (2006.01)
A61B 5/021 (2006.01)

(56) References Cited

U.S. PATENT DOCUMENTS

| | | | |
|---|---|---|---|
| 2011/0257551 A1* | 10/2011 | Banet | A61B 5/0809 600/534 |
| 2012/0112903 A1* | 5/2012 | Kaib | A61N 1/3993 340/539.12 |
| 2014/0312242 A1* | 10/2014 | Valentino | G01P 13/00 250/395 |
| 2016/0094899 A1* | 3/2016 | Aumer | G08B 21/18 340/870.07 |
| 2016/0199002 A1* | 7/2016 | Lee | A61B 5/0008 340/870.07 |
| 2016/0278700 A1* | 9/2016 | Lee | A61B 5/02438 |

* cited by examiner

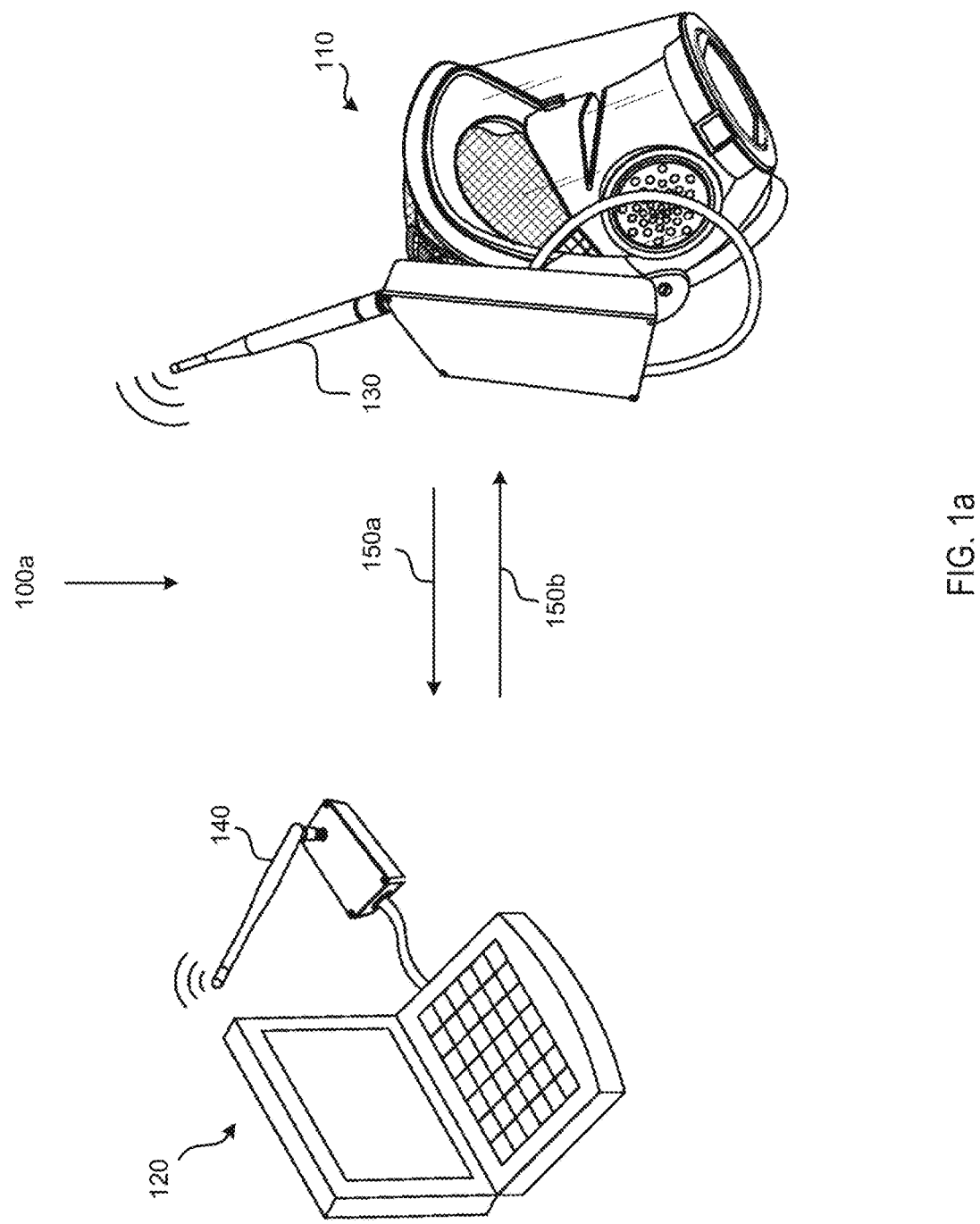

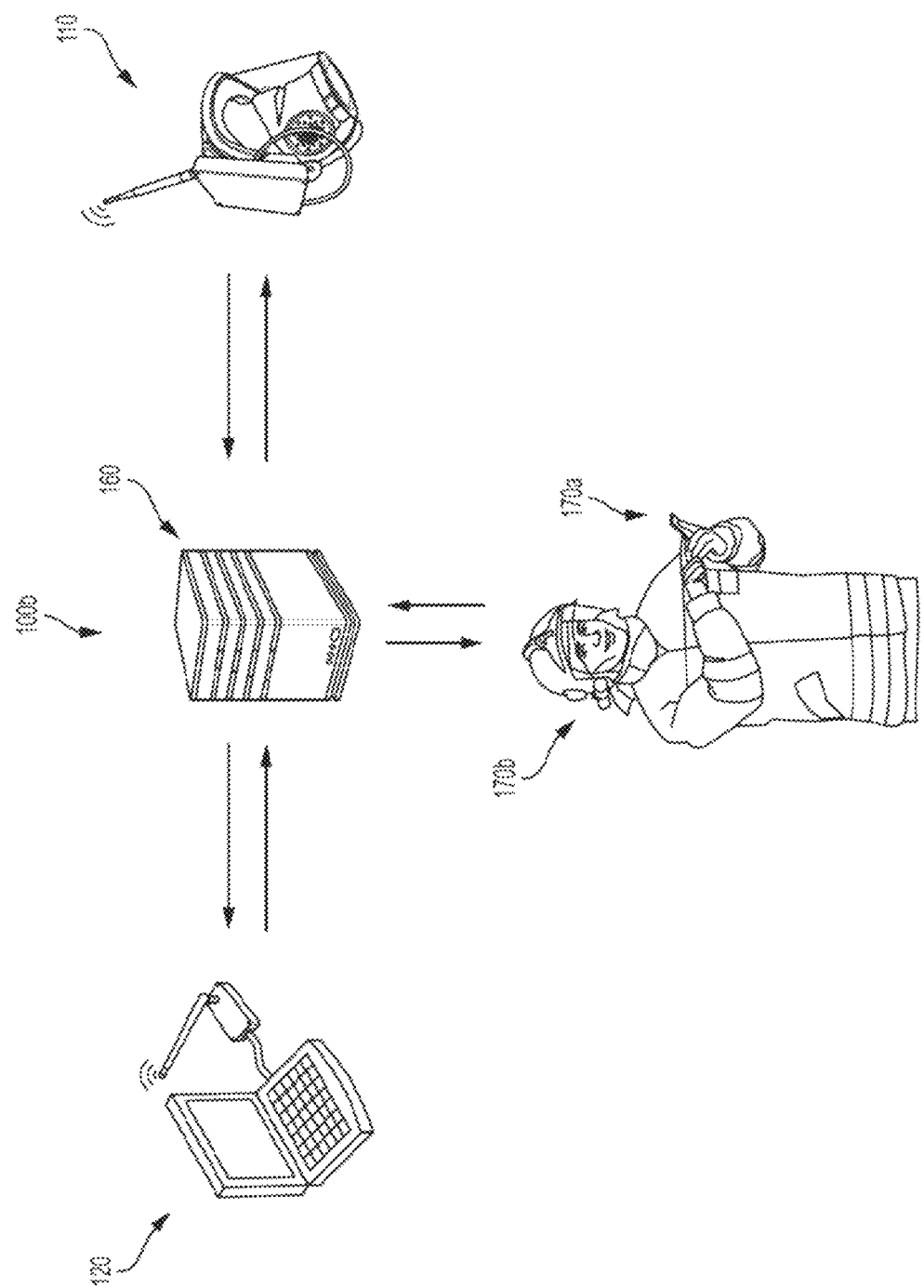

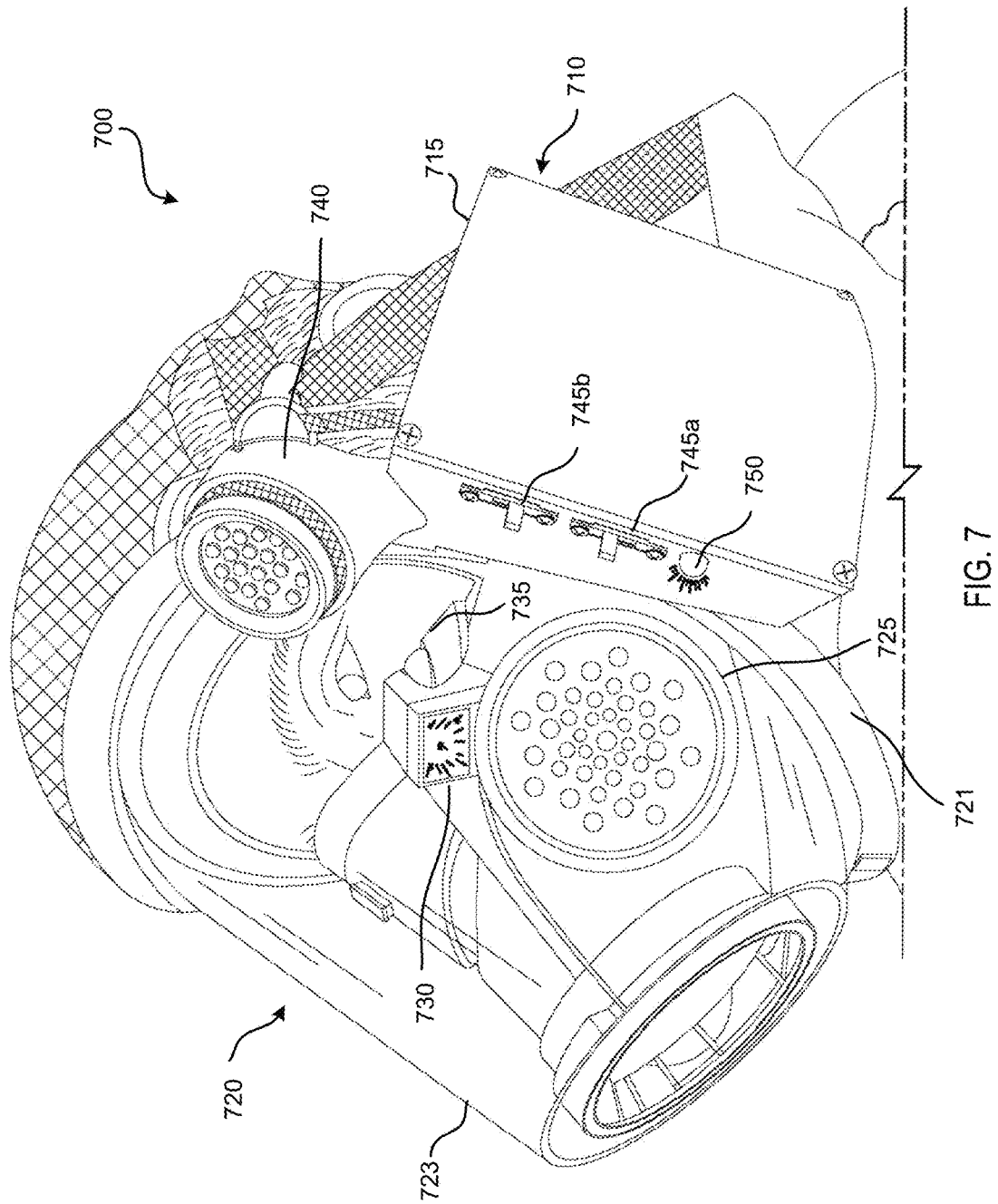

| UNIT # | NAME | STATUS | MESSAGE |
|---|---|---|---|
| 1 | Miller | | — |
| 2 | Clark | ● HIGH HR | Take a rest |
| 3 | Taylor | | — |
| 4 | Kellogg | | — |
| 5 | White | | — |
| 6 | Davis | ● HIGH RR | Fall Back |
| 7 | Lee | | — |
| 8 | Sisk | | — |
| 9 | Walker | | — |

ACTION ITEMS
-Clear Basement
-Chk 3rd FL
-Find Victim on 2nd FL

Current Time: 02:38:45
Elapsed Time: 00:32:24
Squad B

FIG. 14

WEARABLE DEVICES FOR SENSING AND COMMUNICATING DATA ASSOCIATED WITH A USER

CROSS-REFERENCE TO RELATED APPLICATION

This Application claims the benefit, under 35 U.S.C. § 120, of U.S. patent application Ser. No. 15/451,877, filed Mar. 7, 2017, which claims the benefit, under 35 U.S.C. § 119(e), of U.S. Provisional Patent Application No. 62/304,728, filed Mar. 7, 2016, the contents of which are hereby incorporated by reference herein in their entirety as if fully set forth below.

BACKGROUND

When on the job, first responders, such as firefighters, are subject to numerous psychological and physical stressors, including a number of dangerous conditions that may lead to serious injury or even death. However, it is projected that the majority of injuries or fatalities occurring while on the job are caused by overexertion. Overexertion can result from a variety of physiological and atmospheric factors involved in the course of a first responder's duties. As a recognized medical ailment, overexertion can be monitored and indicated by a plurality of biometrics including heart rate, body temperature, and $VO_2$ saturation of a person.

Currently, first responders, such as firefighters, use various personal safety devices to protect against atmospheric stressors. One common safety device is a Self-Contained Breathing Apparatus (SCBA). The SCBA helps to provide breathable air to firefighters in an immediately dangerous environment, such as what is often a smoke-filled environment. While common personal safety devices, such as the SCBA, help mitigate the effects of atmospheric stressors on the human body, they are incapable of providing users with real-time data telling of overexertion, such that a first responder can take control of their health during a stressful situation. It is with respect to these and other considerations that various embodiments of the present disclosure are presented below.

SUMMARY

Embodiments of the present disclosure can include a wearable device for sensing, displaying, and communicating data associated with a condition of a user. In an embodiment, the wearable device can comprise a biometric sensor unit, a display unit, and a control unit. The biometric sensor unit can be configured to sense biometric data associated with a physiological condition of the user. In some embodiments, the biometric sensor unit can comprise one or more sensors configured to sense a plurality of biometrics associated with the physiological condition of the user while using the wearable device. The plurality of biometrics can comprise, for instance, at least one of the user's body temperature, heart rate, $VO2_{max}$, respiration, steps taken, blood pressure, heart rate variability, and calories burnt. In an embodiment, the biometric sensor unit can comprise an earpiece configured to be received by an ear of the user of the wearable device.

The wearable device can also comprise a display unit that can be configured to display at least one visual representation of the sensed biometric data from the biometric sensor unit to the user of the wearable device. In some embodiments, the display unit can comprise at least one of a near-eye display and a heads-up display. In some embodiments, the display unit can be configured to display the at least one visual representation to the user of the wearable device in a location of the wearable device that is clear from obstructing a main view of the user of the wearable device.

The wearable device can also comprise a control unit operatively coupled to the biometric sensor unit and the display unit. The control unit can comprise at least one processor configured to receive indications of the sensed biometric data and cause the display unit to display the at least one visual representation of the biometric data to the user. Additionally, the control unit can comprise at least one communication unit, the communication unit configured to perform at least one of transmitting and receiving information associated with the sensed biometric data to and from a remote unit, respectively.

In some embodiments, the communication unit of the control unit can comprise at least one of a transmitter configured to transmit the biometric data to the remote unit and a receiver configured to receive information from the remote unit, the received information including one or more messages indicating at least one of i) the biometric data associated with the user of the wearable device, ii) action items to be performed by the user of the wearable device, and iii) status messages associated with a condition of the user of the wearable device.

In some embodiments, the condition of the user of the wearable device can comprise a physiological condition of the user of the wearable device while the wearable device is in use.

In some embodiments, the biometric sensor unit, display unit, and control unit can be selectively attachable to headwear of the user of the wearable device.

In some embodiments, the biometric sensor unit and the control unit can comprise one or more sensors configured to sense at least one of the internal or external temperature associated with the wearable device while the wearable device is in use.

Embodiments of the present disclosure can also comprise a system for sensing, displaying, and communicating data associated with a condition of a user of a wearable device. The system can comprise a wearable device, and the wearable device can comprise a biometric sensor unit, a display unit, and a control unit. The biometric sensor unit can be configured to sense biometric data associated with the condition of the user. The display unit can be configured to display one or more visual representations of at least the sensed biometric data from the biometric sensor unit to the user. The control unit can be operatively coupled to the biometric sensor unit and the display unit, and the control unit can be configured to receive indications of the sensed biometric data from the biometric sensor unit and cause the display unit to display the one or more visual representations to the user.

In some embodiments, the system can comprise a remote unit in communication with the wearable device. In some embodiments, the remote unit can comprise a receiver configured to receive the indications of the sensed biometric data from the control unit and a computer-executable application comprising a graphical user interface for interacting with a user of the remote unit.

In some embodiments, the computer-executable application can be stored in a memory coupled to one or more processors and is executable by the one or more processors to perform functions that comprise at least one of: extracting a numerical representation of the sensed biometric data; comparing the numerical representation of the sensed biometric data to a threshold value corresponding to a predetermined biometric range; creating one or more graphical representations of the sensed biometric data for display on the graphical user interface; and generating one or more messages indicating at least one of i) the biometric data associated with the user of the wearable device, ii) action items to be performed by the user of the wearable device, and iii) status messages associated with a condition of the user of the wearable device.

In some embodiments, the one or more messages can be communicated to the control unit of the wearable device, the control unit further configured to communicate the one or more messages to the display unit and the display unit configured to display the information to the user via a visual representation. In some embodiments, the biometric sensor unit can comprise at least one sensor configured to sense a plurality of biometrics associated with the physiological condition of the user while using the wearable device, the plurality of biometrics comprising at least one of the user's body temperature, heart rate, $VO2_{max}$, respiration, steps taken, blood pressure, and calories burnt. In some embodiments, as discussed previously, the biometric sensor unit can comprise an earpiece configured to be received by an ear of the user of the wearable device.

Another embodiment of the present disclosure can comprise a method for sensing, displaying, and communicating data associated with a condition of a user of a wearable device, the method comprising: sensing, by a biometric sensor unit, biometric data associated with a physiological condition of the user, the biometric sensor unit configured to communicate the sensed biometric data to a control unit; receiving, by the control unit, the sensed biometric data, the control unit configured to communicate the biometric data to a display unit; and displaying, by a display unit, at least one visual representation of the sensed biometric data to the user.

In some embodiments, the method can further comprise transmitting, by the control unit, the biometric data to a remote unit; and receiving, by the control unit, one or more messages from the remote unit, the one or more messages including information associated with the biometric data. Additionally, in some embodiments, the method can comprise displaying, by the display unit, the one or more messages to the user of the wearable device.

Similar to that discussed above, the remote unit can comprise a computer-executable application including a graphical user interface for interacting with a user of the remote unit. Additionally, similar to that discussed above, the sensing, by the biometric sensor unit, can comprise sensing, by one or more sensors, a plurality of metrics associated with the physiological condition of the user. In some embodiments, the plurality of metrics comprising at least one of the user's body temperature, heart rate, $VO2_{max}$, respiration, steps taken, blood pressure, and calories burnt while using the wearable device.

BRIEF DESCRIPTION OF THE DRAWINGS

Reference will now be made to the accompanying drawings, which are not necessarily drawn to scale.

FIGS. 1a and 1b illustrate systems for sensing, displaying, and/or communicating a plurality of data corresponding to a user, in accordance with an embodiment of the present disclosure.

FIG. 7 illustrates another embodiment of a wearable device for sensing, displaying, and/or communicating a plurality of data corresponding to a user, in accordance with the present disclosure.

FIG. 14 is another illustration of a graphical user interface of a computer-executable application, in accordance with an embodiment of the present disclosure.

DETAILED DESCRIPTION

Figure 2A:
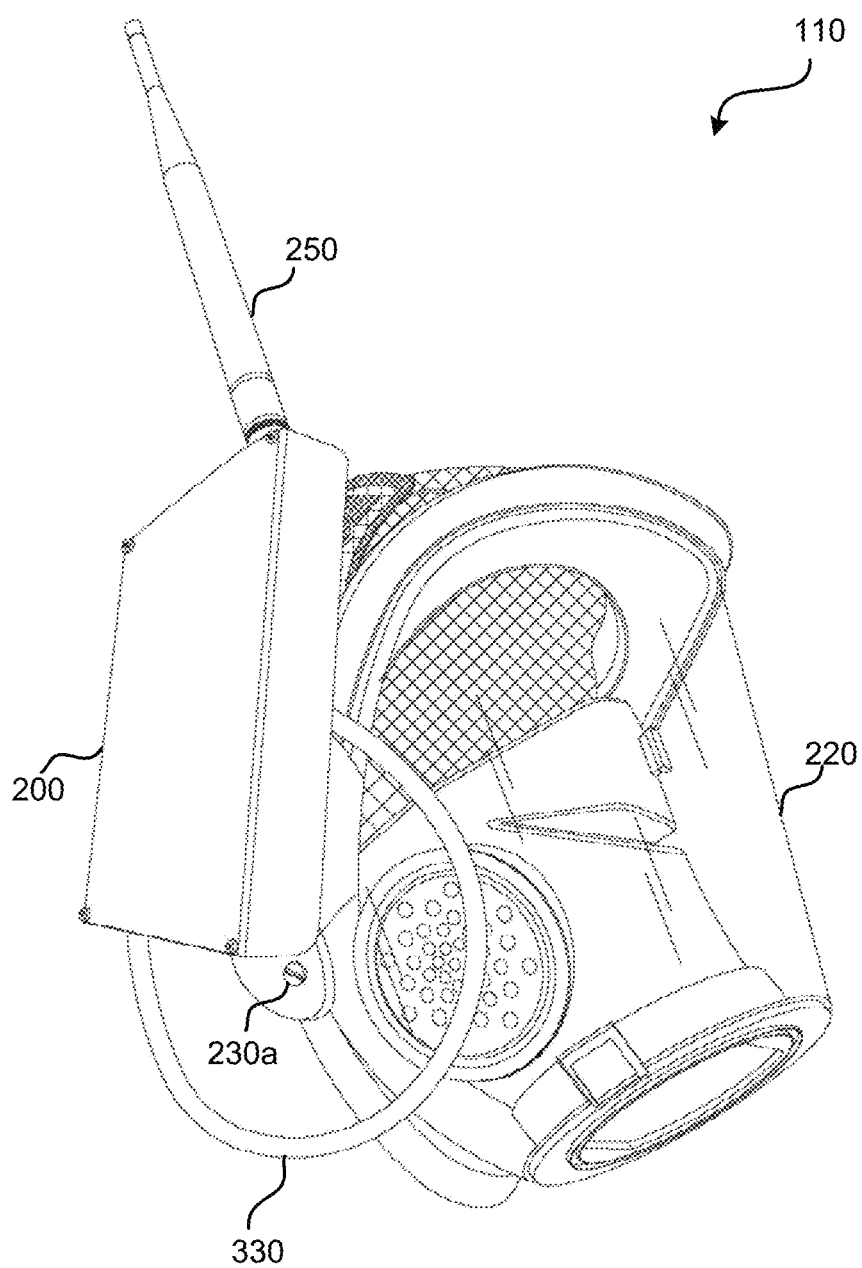
FIG. 2a illustrates an embodiment of a wearable device attached to headwear, in accordance with the present disclosure.

In some aspects, the present disclosure relates to wearable devices for detecting, displaying, and communicating data associated with a user. Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

A detailed description of aspects of the present disclosure, in accordance with various example embodiments, will now be provided with reference to the accompanying drawings. The drawings form a part hereof and show, by way of illustration, specific embodiments and examples. In referring to the drawings, like numerals represent like elements throughout the several figures.

In some aspects, the present disclosure can relate to systems for sensing, displaying, and/or communicating a plurality of data associated with a condition of the user. FIGS. 1a and 1b illustrate exemplary systems 100a, 100b for sensing, displaying, and/or communicating a plurality of data corresponding to a user. As illustrated at FIG. 1a, a wearable device 110 can be in communication with a remote unit 120. The wearable device 110 can be configured to sense biometric data associated with a condition of a user of the wearable device 110 and can comprise a communication unit 130 configured to transmit indications of the biometric data along a transmission pathway 150a to the remote unit 120. The remote unit 120 can be configured to receive the indications of the biometric data from the wearable device 110 via a remote communication unit 140. The remote unit 120 can be further configured to transmit information (e.g. one or more messages) along a transmission pathway 150b to the wearable device 110.

In some embodiments, as illustrated at FIG. 1a, the communication unit 130 and the remote communication unit 140 can be corresponding antenna units. For example, the wearable device can comprise a communication unit 130 attached thereto that is an antenna that transmits a signal, and the remote unit 120, which can include a computer, can be operatively connected to a corresponding communication unit 140 (e.g. through a USB port), that can be an antenna that can transmit a signal. Such interaction can, for instance, facilitate tracking and monitoring of a user's wellbeing or activity while the user is wearing the wearable device 110, by facilitating the transfer of relevant data between the wearable device 110 and the remote unit 120.

In other embodiments, the communication unit 130 and the remote unit 120 can comprise a cell phone chip enabling connecting, transmitting, and receiving data via a cellular network. The cell phone chip can include any telecommunications technology currently available, including GSM, 3G, or 4G systems, or subsequently developed.

FIG. 1b illustrates an exemplary system 100b and corresponding process for sensing, displaying, and communicating data associated with a condition of the user. The system 100b can comprise a wearable device 110, a server 160, a remote unit 120, and mobile device 170a used by a mobile user 170b. As shown in FIG. 1b, the wearable device 110, remote unit 120, and mobile device 170a can communicate with each other through the server 160. The mobile user 170b can be, for instance, a past or future user of the wearable device 110.

As illustrated at FIG. 1b, transmission pathways can comprise a mobile user device 170a setting initial calibration data for when the mobile user 170b uses the wearable device 110. In some embodiments, the calibration data can include personal information about the mobile user 170b including but not limited to height, weight, age, and gender. Additionally, in some embodiments, each wearable device 110 may receive a unique identification number and may be recognized by a computer-executable application running on a computer of the remote unit 120, based on that identification number. Therefore, when a mobile user 170b is initially calibrating the wearable device 110, the mobile user 170b can input the unique identification number corresponding to the wearable device 110, thereby linking the mobile user's 170b profile with the wearable device 110. Associating a mobile user's 170 profile with an identification number of the wearable device 110 can permit various users to use the same wearable device 110. When the wearable device 110 is calibrated, the wearable device 110 can correspond with the specific mobile user 170b who will wear the wearable device 110 and calculate and transmit biometric data specific to that user.

The wearable device 110 can be in communication with the remote unit 120. For instance, as discussed previously, the wearable device 110 can detect data associated with a condition of a user and transmit that data to the remote unit 120. As illustrated in FIG. 1b, a server 160 can serve as an intermediary between the wearable device 110 and the remote unit 120. The remote unit 120 can be configured to receive the data from the server 160, and in some embodiments, display such data to a remote user accessing the remote unit via a computer-executable application. Additionally, the remote unit 120 can be configured to transmit information to the wearable device 110, which can include one or more messages. The server 160 can act as an intermediary between the remote unit 120 and the wearable device 110 and transmit the information to the wearable device 110.

In other embodiments (not shown), the wearable device 110 can communicate directly to the remote unit 120 without interfacing through the server 160. Following, the remote unit 120 can be in communication with the server 160 for the purpose of storing or otherwise communicating data associated with the user of the wearable device.

Figure 2B:
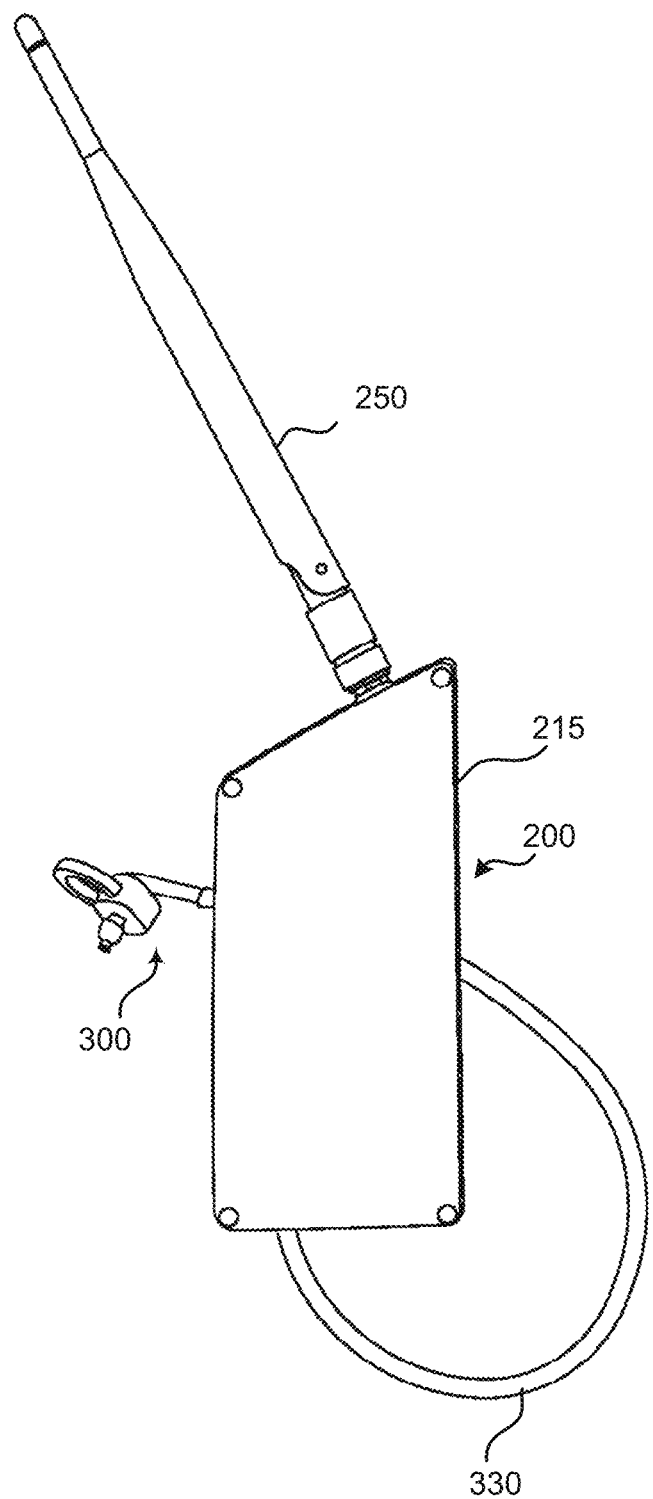
FIG. 2b illustrates a control unit of the wearable device, in accordance with an embodiment of the present disclosure.
Figure 2C:
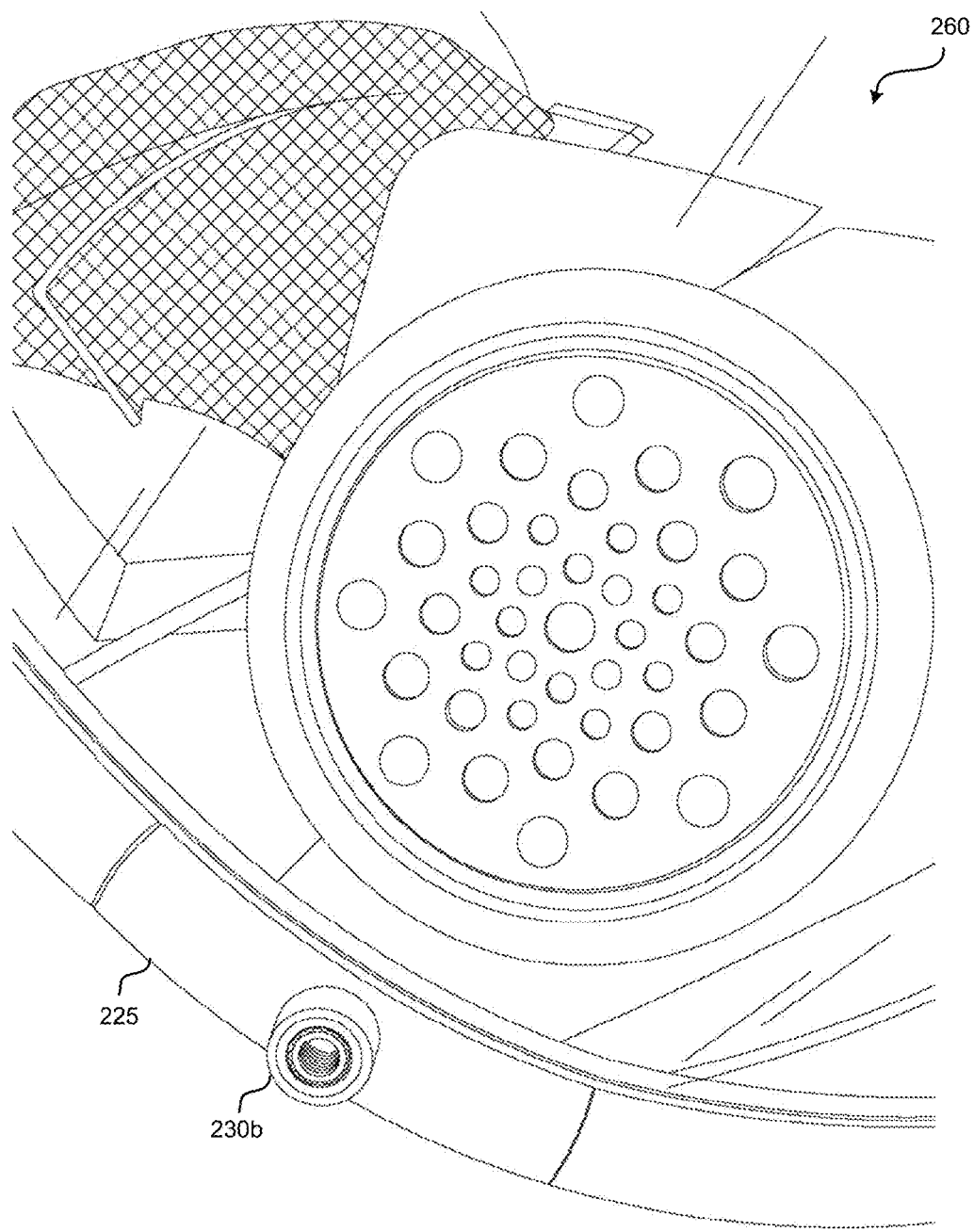
FIG. 2c illustrates an attachment interface for attaching the control unit to headwear, in accordance with an embodiment of the present disclosure.
Figure 3A:
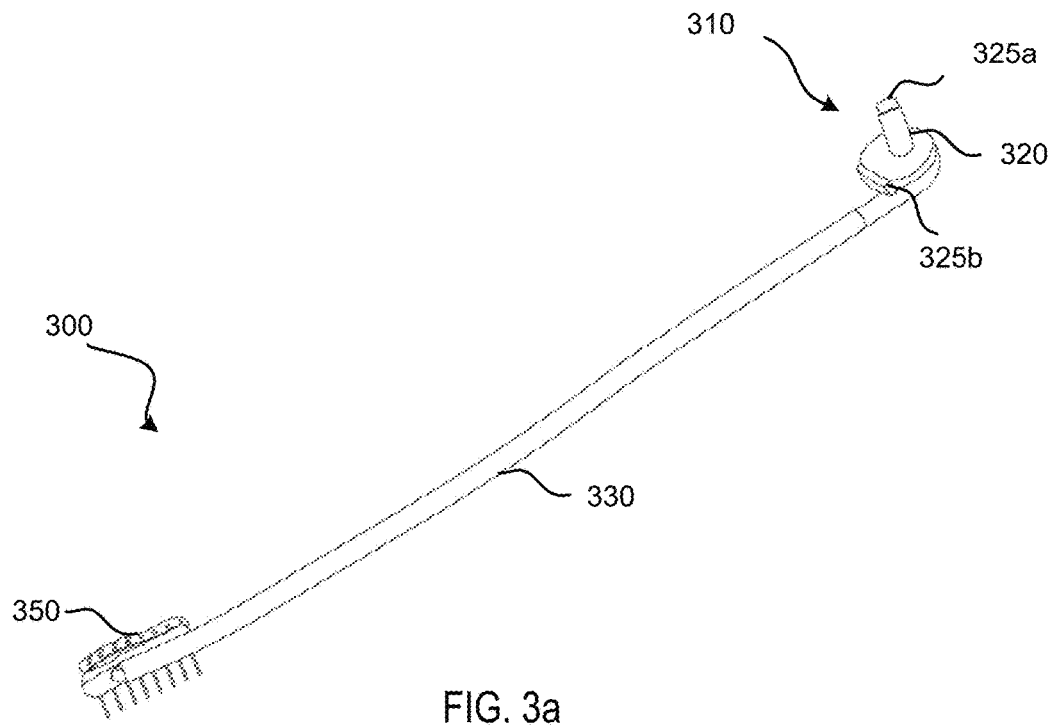
FIGS. 3a and 3b illustrate a biometric sensor unit comprising a biometric earpiece, in accordance with an embodiment of the present disclosure.
Figure 3B:
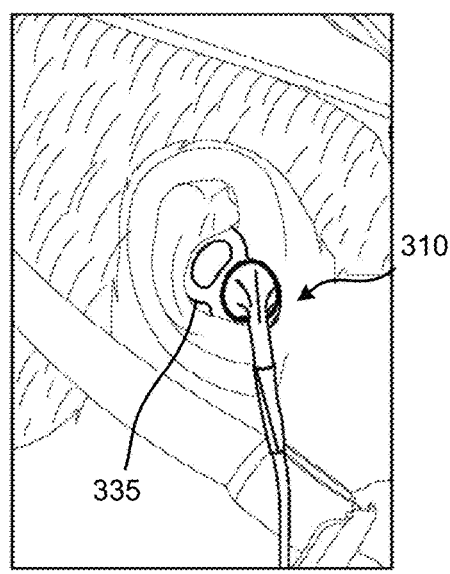
Figure 4:
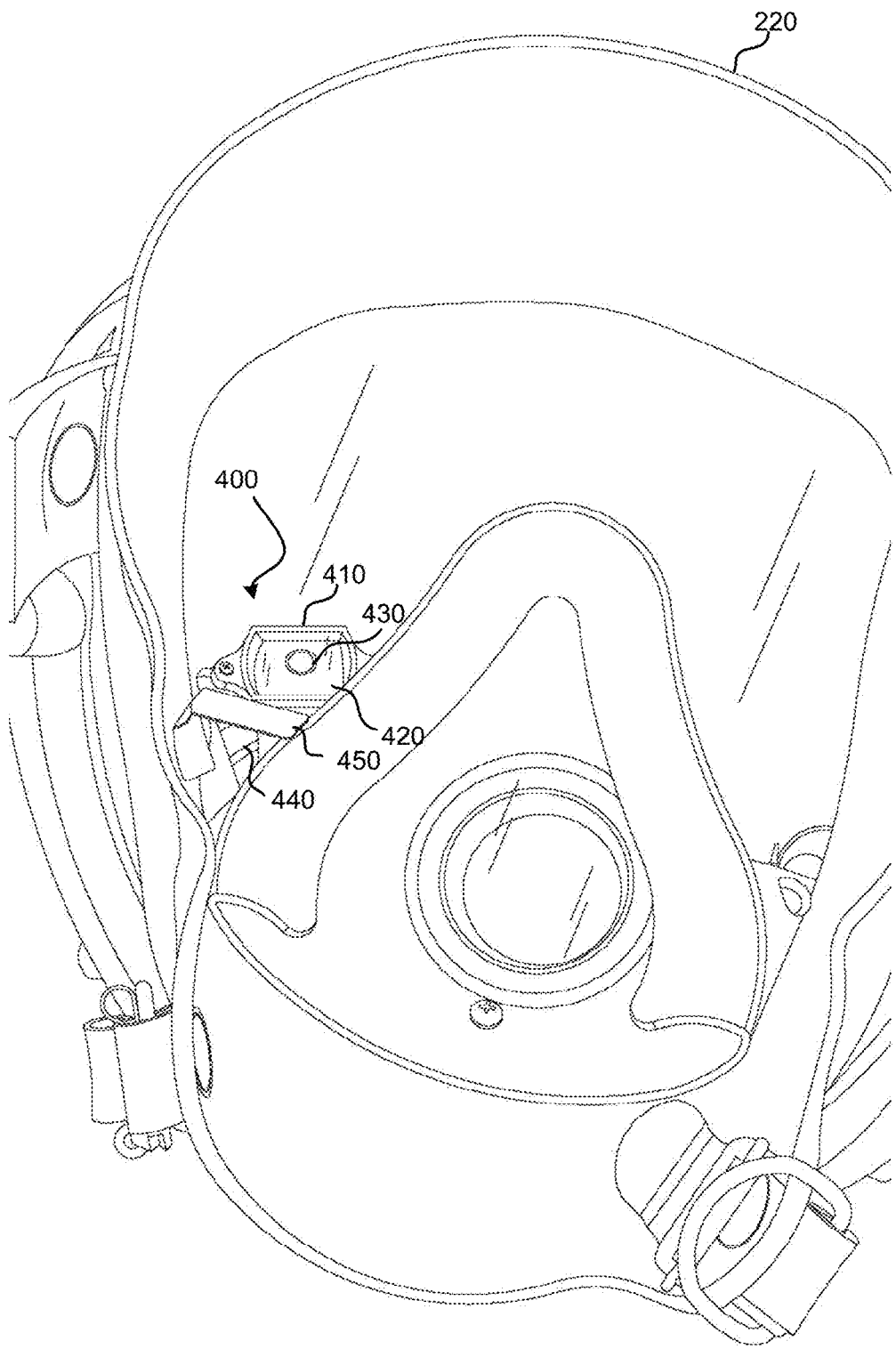
FIG. 4 illustrates a display unit of the wearable device, in accordance with an embodiment of the present disclosure.
Figure 5:
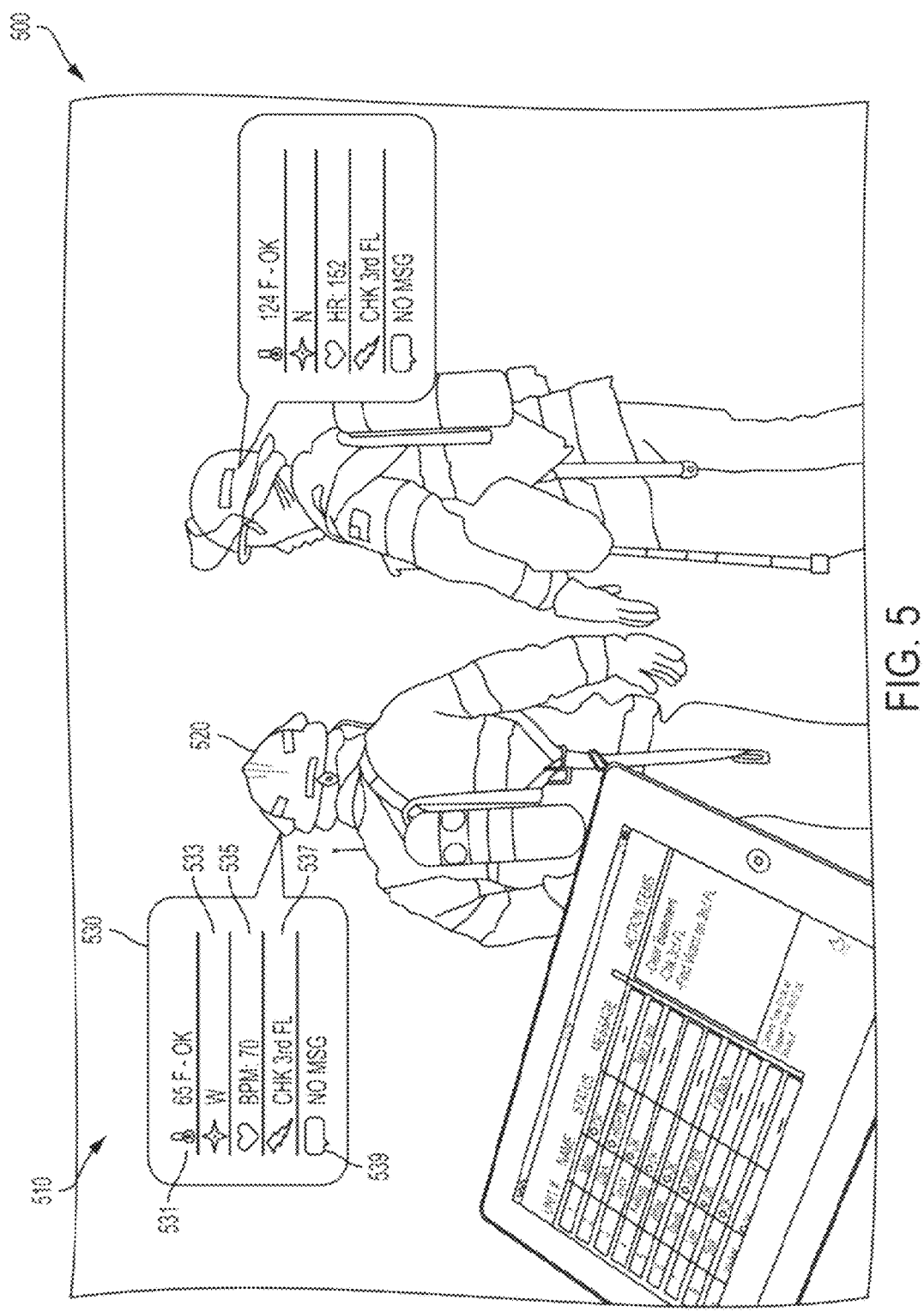
FIG. 5 illustrates an implementation of systems and devices with users of wearable devices according to embodiments of the present disclosure.

FIGS. 2a-2c, 3a, 3b, and 4 illustrate aspects of the present disclosure include a wearable device 110 for sensing, displaying, and/or communicating a plurality of data associated with a condition of a user of the wearable device 110. As illustrated in 2a-2c, 3a, 3b, and 4, the wearable device 110 can comprise a control unit 200 (FIGS. 2a-2c), a biometric sensor unit 300 (FIGS. 3a and 3b), and a display unit 400 (FIG. 4). The control unit 200 can be integrally connected with or selectively attached to headwear 220 worn by a user and can comprise an attachment interface 230a, 230b, as illustrated in FIGS. 2a-2c. In some embodiments, the headwear 220 worn by a user can be a SCBA. As illustrated in FIGS. 3a-3b, the biometric sensor unit 300 can comprise a plurality of biosensors (325a, 325b) capable of detecting a plurality of conditions indicative of a state of the user's body while the user is wearing the wearable device 110. In some embodiments, the biometric sensor unit 300 can comprise an ear-receiving portion 310 wearable on and/or in the user's ear, as illustrated in FIGS. 3a-3b. As illustrated in FIGS. 4 and 5, in some embodiments, the display unit 400 can be positioned within a field of view of the user and provide a visual representation of the biometric data and/or other information to the user.

FIGS. 2a and 2b illustrate an exemplary embodiment of a control unit 200 for use in a wearable device 110. In some embodiments, a biometric sensor unit 300 can be connected to the control unit 200 via a wire 330. Aspects of the biometric sensor unit 300 will be discussed in greater detail with respect to FIGS. 3a-3b.

As shown in FIG. 2b, the control unit 200 can comprise a housing 215 containing a variety of hardware and devices for controlling and directing information flow as well as tracking other relevant metrics associated with the user of the wearable device. Additionally, in some embodiments, the control unit 200 can comprise an external or internal antenna. For example, FIGS. 2a-2b illustrate an external antenna 250 attached to the control unit 200, in accordance with an embodiment of the present disclosure. The external antenna 250 can permit transmission of data acquired by the wearable device 110 to a remote unit 120, such as that illustrated in FIGS. 1a-1b.

Figure 6:
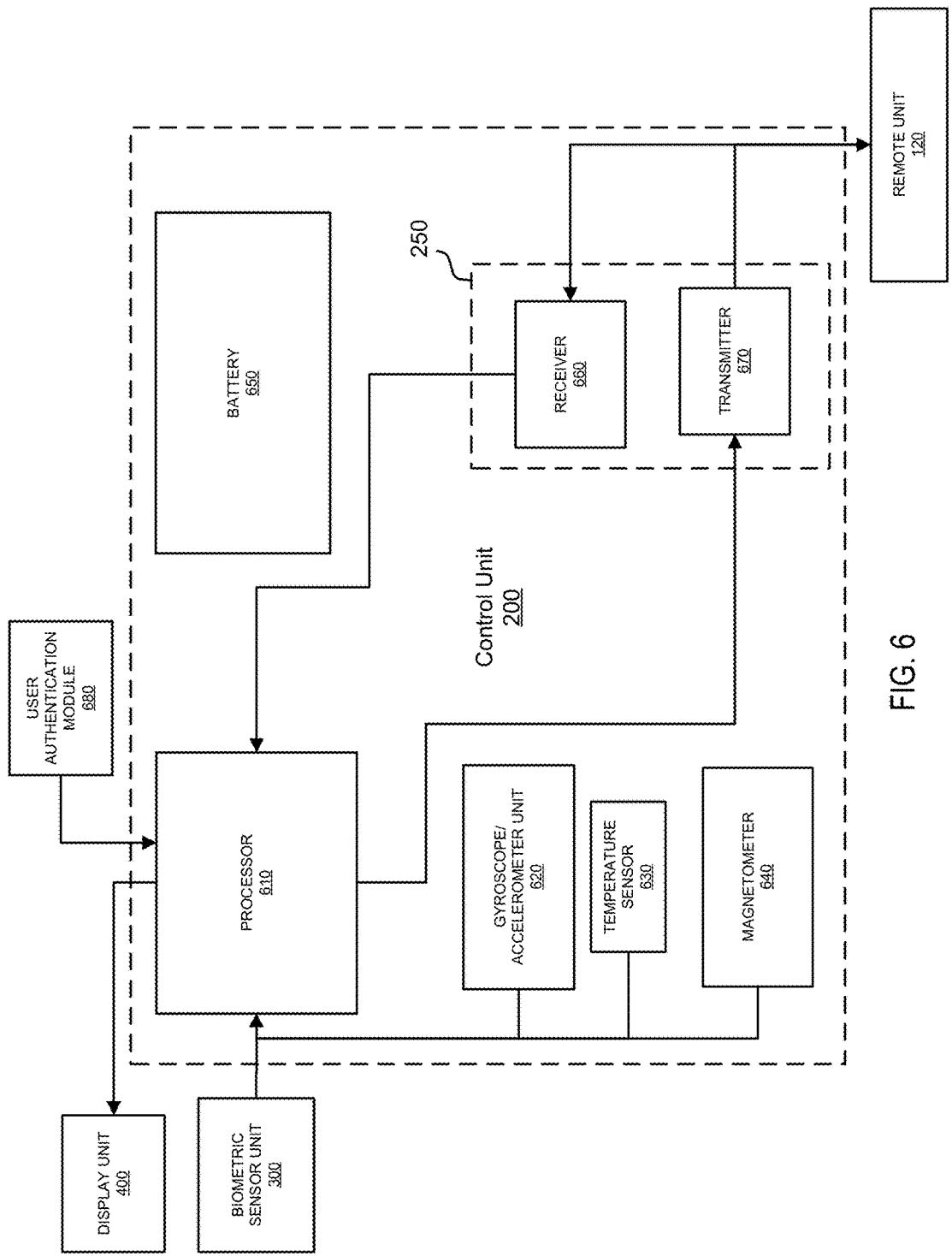
FIG. 6 illustrates exemplary architecture of a control unit interacting with other components of the wearable device and a remote unit, in accordance with an embodiment of the present disclosure.

The housing 215 can contain a variety of hardware and devices (illustrated in greater detail at FIG. 6). For instance, the housing 215 can include one or more of a microcontroller (e.g., one or more programmable computer processors), magnetometer, gyroscope, accelerometer, radio (comprising one or more antennas), battery, one or more buses, and one or more temperature sensors. Additionally, the housing 215 of the control unit 200 can be made of any suitable material currently available or subsequently developed that is sufficiently durable for a variety of uses. In an embodiment for use within a very hot area, the housing 215 can be made out of a material that can provide heat-resistance. For instance, the material can be one or more of Teflon, fiberglass, and high-temperature epoxy. In other embodiments, the housing 215 can be made of a flame-retardant material.

FIG. 2c illustrates an exemplary attachment interface 260 for attaching the control unit 200 to the headwear 220, in accordance with an embodiment of the present disclosure. The attachment interface can comprise a socket 230b that can receive a corresponding fastener 230a (as shown in FIG. 2a). The socket 230b can be embedded into a frame 225 of the headwear 220. The attachment interface 260 can allow for attaching the control unit (shown in FIGS. 2a-2b) to headwear 220.

FIGS. 3a and 3b illustrate an exemplary biometric sensor unit 300 comprising a biometric earpiece configured to be received by an ear of the user of the wearable device. The biometric sensor unit 300 can be any device comprising a plurality of sensors capable of sensing biometric data associated with the user. For instance, in some embodiments, as illustrated at FIG. 3a, the biometric sensor unit 300 can comprise a plurality of sensors (325a, 325b) for sensing biometric data associated with a physiological condition of the user. While embodiments of the biometric sensor unit 300 are illustrated in the drawings as a biometric earpiece, it is understood that the biometric sensor unit can comprise other devices (wearable or not) capable of sensing biometric data associated with a physiological condition of the user. Additionally, the plurality of sensors integrated with the biometric sensor unit can be a variety of sensors capable of detecting data associated with a condition of the user, including electro-optical sensors, thermal sensors, oxygen sensors, moisture sensors, and/or biosensors.

As illustrated in FIG. 3a, the biometric earpiece can comprise an ear-receiving portion 310 having an ear interface 320. Additionally, one or more sensors 325a, 325b can be integrated with the ear-receiving portion 310 to detect a plurality of data associated with a condition of the user. In some embodiments, the ear-receiving portion 310 can comprise one or more sensors 325b located in a lower portion of the ear-receiving portion and one or more sensors 325a located proximate the ear interface 320. For example, a plurality of sensors 325b detecting the heart rate, the $VO_{2max}$, heart rate quality signal, and steps can be integrated in the lower portion of the ear-receiving portion 310 and a digital temperature sensor 325a can be integrated in the ear interface 320. In some embodiments, the plurality of sensors integrated in the ear-receiving portion 310 can be Valencell's PerformTek® sensor. In other embodiments, the plurality of sensors 325a, 325b integrated with the ear-receiving portion 310 can be one or more optical sensors. Additionally, in some embodiments, the ear-receiving portion 310 can comprise a speaker to serve a variety of purposes, including amplification of external sounds or communications from remote users, or a plurality of moisture sensors. In other embodiments, the ear-receiving portion can comprise a bone conduction microphone to, for instance, transmit the user's voice to the remote user.

In some embodiments, the biometric sensor unit 300 can comprise a biometric earpiece having an ear-receiving portion 310 that can be configured to fit snugly within the user's ear, as illustrated at FIG. 3b. For instance, in some embodiments, the ear-receiving portion 310 can include a flexible ring 335 attached proximate an upper portion of the ear-receiving portion 310. In some embodiments, the flexible ring 335 can comprise a resilient material to maintain a snug fit within the user's ear, as illustrated at FIG. 3b. In other embodiments, the biometric earpiece can comprise an over the ear loop (not shown) that fits behind the user's ear and assists with holding the earpiece in place.

Additionally, the biometric sensor unit 300 can be operatively connected with the control unit 200. In embodiments comprising a biometric earpiece, as illustrated at FIG. 3a, the biometric earpiece can comprise a wire 330 extending from the ear-receiving portion 310 and connecting with the control unit 200 via an electrical connector 350. As such, the biometric earpiece can relay the data detected by the sensors 325a, 325b to the control unit 200. For instance, in an embodiment, the biometric sensor unit 300 can be connected to the control unit 200 by a simple wire that connects to a Japanese solderless terminal (JST) bus. Additionally, to improve resistance to atmospheric factors, the wire 330 of the biometric sensor unit 300 can be coated in a flame-retardant or high-temperature epoxy or silicon sleeving to protect the wire 330.

While embodiments of the biometric sensor unit 300 described above can use a wired connection between the biometric sensor unit 300 and the control unit 200, the biometric sensor unit 300 can be in wireless communication with the control unit 200. For example, in some embodiments, the biometric sensor unit 300 can include, for instance, a Bluetooth device for providing wireless communication between the biometric sensor unit 300 and the control unit 200.

FIG. 4 illustrates an exemplary display unit 400 mounted within headwear 220 worn by a user. The display unit 400 can comprise any device capable of displaying information to a user. In some embodiments, the display unit 400 can comprise a near-eye display capable of displaying a variety of information to the user of the wearable device. In other embodiments, the display unit 400 can comprise a heads up display capable of displaying a variety of information to the user of the wearable device. In other embodiments, the display unit 400 can display the information on a semi-transparent surface, like a screen or the visor of the headwear. Other optical systems that can be incorporated in the display unit 400 include a virtual reality display, eye tracking, head tracking, a head-mounted display, display magnification, and/or an optical head-mounted display.

As illustrated at FIG. 4, the display unit 400 can be mounted within a field of view of the user and can be positioned proximate the wearer's eye(s) when the wearer is wearing headwear 220. The display unit 400 can comprise a casing 410, a screen 420, and an optical display system 430 (showing a lens, the remainder of the optical display system not shown) for displaying information to the user. For instance, as illustrated at FIG. 4, the display unit 400 can be mounted on a left-most portion of the interior of the headwear 220, relative to the user of the wearable device 110. As such, the display unit 400 and the information displayed thereon can be visible in the left eye of the user. Those skilled in the art will understand that mounting the display unit 400 in a side portion of the headwear 220 can avoid obstructing the user's view. In other embodiments, however, the display unit 400 can be mounted on the right-most portion of the headwear 220 or on both side portions of the headwear 220.

In some embodiments, the display unit 400 can comprise a near-eye display. Near-eye displays can utilize the human eye for up-close image display such that the human eye acts as the last element in the optical chain with a final image being created on the eye's retina. The near-eye display can generally comprise a virtual image, a microdisplay, and a lens. The lens of the near-eye display can provide magnification of the virtual image to the user of the near-eye display. Additionally, the microdisplay contained within the near-eye display can comprise a waveguide optical element that collects light at the input and relays it towards the user's eye. In some embodiments, the near-eye display can comprise additional components for minimizing latency, maximizing optical contrast, and maximizing the field of view.

In some embodiments, the display unit 400 can comprise a heads-up display. In embodiments incorporating a heads-up display, the heads-up display can comprise a projector unit, a combiner, and an optical display system. The projector unit can comprise an optical collimator including a convex lens or a concave mirror and a lighting element. For example, the lighting element can comprise LEDs or backlight sources. In some embodiments, the combiner can comprise a beam splitter. In some embodiments the optical display system can comprise a computer unit incorporating a receiver for receiving information to be displayed to the user.

In some embodiments, the display unit 400 can be mounted to the headwear 220 using an adjustable, flexible or semi-flexible member 440 such as a wire (e.g., selectively bendable copper wire). The adjustable member 440 can permit the user to adjust the display unit 400 within the headwear 220 to make slight adjustments and clear the user's line of sight. Mounting the display unit 400 in line with the user's eyes can have the added advantage of not obstructing the user's view of the floor or ceiling, for instance. Additionally, those skilled in the art will understand that the display unit 400 can be mounted within the interior of the headwear 220 in a variety of ways, including adhesive, hook and loop fasteners, or other adjustable mounting elements composed of other suitable materials, other than copper.

In some embodiments, to connect the display unit 400 with the control unit 200, a high temperature ribbon cable 450 attached to the display unit 400 can be navigated through the headwear 220 and integrated with the control unit 200. In some embodiments, the display unit 400 can comprise a UART bus controllable by the processor. In other embodiments, the display unit 400 can be connected to the control unit 200 using Bluetooth or other similar wireless technology.

In another embodiment, the display unit 400 can be incorporated into the outer housing of the control unit 200. In such an embodiment, the display unit can comprise one or more indicator lights that communicate with the user if certain biometrics are within a normal or risky range. For instance, in some embodiments, the display unit can comprise two indicator lights, one green and one red. If the green indicator light is lit up, then that will indicate to the user that all biometrics are in a normal range. If the red indicator light is lit up, this will indicate to the user that some or all biometrics are exceeding the normal level and indicative of a warning that the biometric is approaching a dangerous or unhealthy level.

FIG. 5 illustrates an implementation 500 of certain aspects of systems and devices in accordance with embodiments of the present disclosure. FIG. 5 illustrates a visual representation 510 that a user 520 wearing the wearable device may view using the display unit 400. As illustrated at FIG. 5, the display unit, such as that illustrated in FIG. 4, can display a variety of information 530 to the wearer 520 in an abbreviated format. For instance, the display unit 400 can show life-critical data to the user including the ambient temperature surrounding the user, the current battery level of the device, the compass heading the user is facing, a biometric data line, sensor readings, action items, and/or personal text messages (see also FIGS. 12-14). In an embodiment, as illustrated at FIG. 5, the display unit 400 can provide the user 520 with the ambient temperature 531, the user's compass direction 533, the user's heart rate 535, action items 537, and messages 539.

In some embodiments, an ambient temperature reading can be useful in detecting flashover events. In some embodiments, the text messages can be from a remote user to the user of the wearable device, for example messages regarding the wellbeing of the user of the wearable device 110. The action items can be, for instance, sent from a remote user accessing a device incorporating a communication unit, as illustrated at FIGS. 1a-1b, which can transmit a message receivable by a radio unit incorporated within the wearable device 110. In some embodiments, the action items and personal message areas can incorporate scrolling text if the message received is above a particular character limit. For instance, the scrolling text can incorporate automated scrolling functionality. In some embodiments, the biometric data line displays the heart rate, pulse, oxygenation level, and respiratory rate of the user of the wearable device. In some embodiments, the display unit can cycle through a plurality of displays incorporating different information. It should be appreciated that having an integrated display unit in the wearable device, as described above, can allow for real-time monitoring of a variety of biometrics as well as incorporate communication functionality, essential for receiving commands, instructions, or other messages.

Additionally, in some embodiments, the display unit 400 can cycle through various combinations of metrics or messages over time. Other metrics that the display unit 400 can provide to the user 320 may include body temperature, heart rate, external temperature, $VO2_{max}$, heart-rate variability, signal level of the wearable device 110, battery level of the wearable device 110, and/or blood pressure.

FIG. 6 is an exemplary diagram of the interior of the control unit 200. The control unit 200 can comprise a housing 215 that may contain one or more of a processor 610, a gyroscope and accelerometer unit 620, one or more temperature sensors 630, one or more magnetometers 640, a battery 650, and a communication unit including a receiver 660 and a transmitter 670. In some embodiments the processor 610 can be a microcontroller comprising one or more programmable computer processors. In some embodiments, the receiver 660 and the transmitter 670 can comprise one or more antennas. In addition to the components illustrated in FIG. 6, the control unit 200 can comprise various other devices including one or more buses, various other sensors, and other electrical components.

As illustrated at FIG. 6, in some embodiments, the processor 610 can control and direct the flow of information from the sensors located in the biometric sensor unit 300 and the other devices housed within the control unit 200, such as the gyroscope/accelerometer unit 620, the temperature sensor 630, and the magnetometer 640, or other additional sensor unit or device known in the art. Additionally, the processor 610 can control and direct the flow of information to and from the transmitter 670 and the receiver 660, respectively, permitting communication with a remote unit or server. The processor 610 can further control and direct the flow of information to the display unit 400.

The processor 610 can be any microcontroller, for example Teensy++. The magnetometer 640 can be any suitable magnetometer that can, for instance, include a three-axis sensor that can detect Earth's magnetic field to provide a compass heading. The gyroscope/accelerometer unit(s) 620 can comprise any gyroscope that includes a three-axis angular rate sensor and the accelerometer 620 can be any accelerometer that includes a three-axis sensor that can detect acceleration. The gyroscope and accelerometer data can be combined to deduce the yaw, tilt, and roll of the housing on the side of the headwear. The yaw, tilt, and roll can then be normalized and calibrated with the magnetometer data to give an accurate compass heading despite the orientation of the magnetometer 640. In other embodiments, the processor can be configured to determine the geo-location using the radio signal. Additionally, the processor can be configured for indoor tracking or triangulation. For instance, the control unit 200 can trace or track the movements of a user throughout an area.

The temperature sensor 630 can serve a variety of functions, including monitoring the temperature inside the housing 215 of the control unit 200 to determine if the inside of the housing 215 is cool enough for the processor 610 to be in an operating state and also monitoring the ambient temperature around the user. In some embodiments, if an unsafe temperature inside the housing 215 is reached, the control unit 200 can be configured to shut down. The temperature sensor that can detect the ambient temperature surrounding the user can be exposed to the atmosphere around the control unit. For example, the temperature sensor can be exposed through a small hole in the housing.

Additionally, the control unit 200 can be in communication with a variety of devices including the biometric sensor unit 300, the display unit 400, a remote server, and a remote unit (as shown in FIGS. 1a and 1b). To allow the wearable device 110 to communicate with, for instance, a server and a remote unit, the control unit 200 can include a communication unit 250 comprising a receiver 660 and a transmitter 670. In some embodiments, the communication unit 250 can comprise a radio unit, such as the Xbee Pro Series 1 60 mW Wire Antenna. This radio unit can operate at 3.3 V at a current value of 215 mA, with a range of one mile. The radio unit can use the 802.15.4 IEEE standard for packet transmission. The data gathered by the processor 610 can be transmitted back to a remote user using the communication unit 250 via the transmitter 670 and information from the remote unit or server can be received by the control unit at the receiver 660.

FIG. 7 illustrates another embodiment of a wearable device 700 in accordance with the present disclosure. As shown, the wearable device 700 can be worn concurrently with headwear 720. The wearable device 700 can comprise a control unit 710, a biometric sensor unit (not shown, but similar to that illustrated in FIG. 1d), and a display unit 730. The control unit 710 can comprise a housing 715 mounted to a side of the headwear 720. For instance, the housing 715 can be integrally connected to the headwear 720 and thereby comprise an attachment interface (not shown, but similar to that illustrated in FIG. 1c). The attachment interface can comprise a fastener, such as a screw, that can engage a corresponding socket thereby attaching the housing 715 to the headwear 720. As illustrated in FIG. 7, the control unit 710 can attach to a left side of the headwear 720 on a frame 721 surrounding the visor 723. The control unit 710 can be sized and positioned so as not to block the user's visibility or components of the headwear 720, such as mechanical speaking diaphragms 725 in the headwear 720. To attach the control unit 710 to the headwear 720 as such, a socket can be embedded in the frame 721 of the headwear 720 on the left side (relative to the user). In other embodiments, however, the control unit 710 can be positioned on a right side of the headwear 720 and include a fastener in the frame 721 on the right side of the headwear 720.

Some embodiments of the wearable device 700 as illustrated at FIG. 7 can incorporate a biometric sensor unit, such as that illustrated in FIGS. 3a-3b, and a display unit 730. Therefore, the biometric sensor unit and the display unit 730 can comprise some or all of the features discussed above. As illustrated at FIG. 7, and similarly to FIG. 4, the display unit 730 can be located within the interior of the headwear 720 near at least one eye of the user and can include an adjustable member 735 (such as a wire) that can be used for adjusting the position and/or location of the display unit 730 relative to an eye of the user. Additionally, the wearable device 700 can comprise a plurality of add-ons allowing a user to interact with the device 700 attached to the control unit 710. For instance, the add-ons can include a light 740 or thermal imaging camera to assist with visibility in front of and around the user. Additionally, the control unit 710 may comprise a plurality of switches 745a, 745b for turning the wearable device 700 on and off and/or the additional light 740. Additionally, in some embodiments, the control unit 710 can comprise an indicator light 750 that will light up upon turning on the wearable device 700.

Figure 8A:
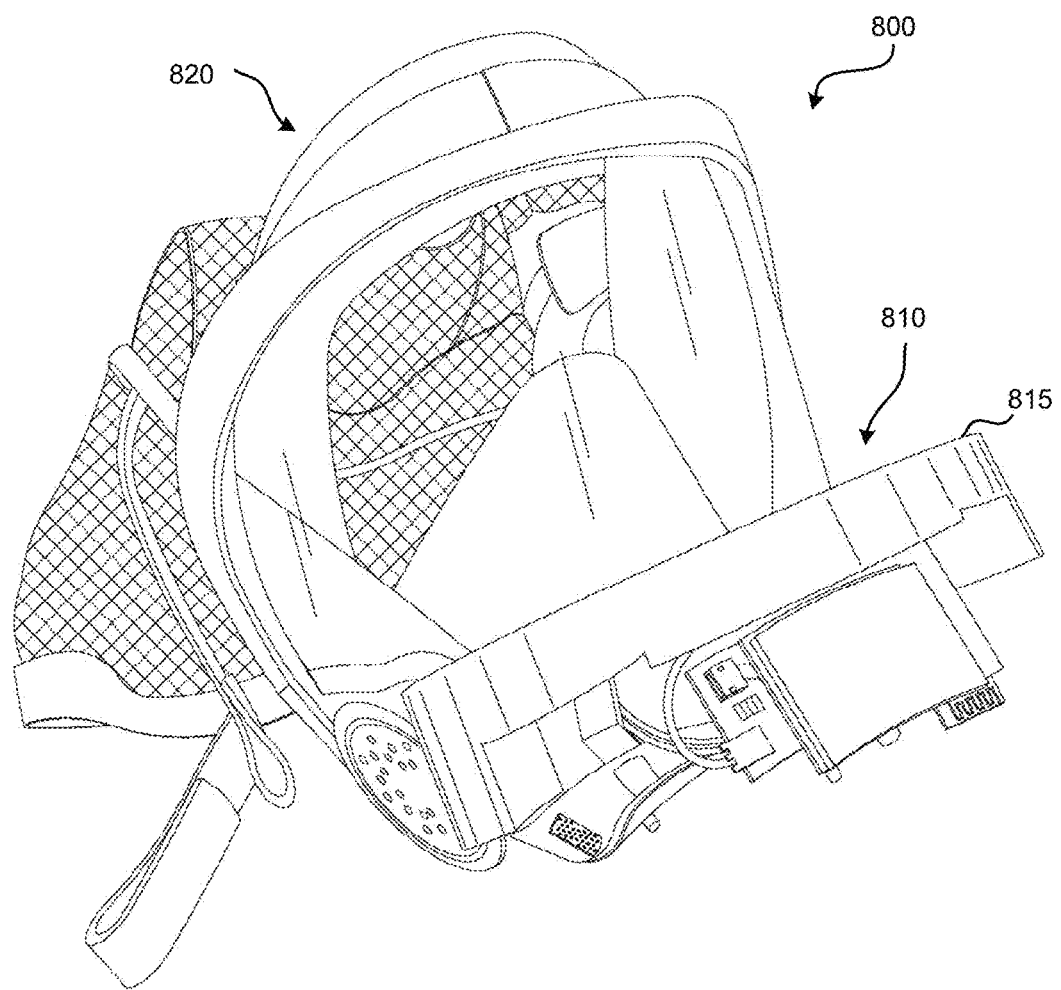
FIGS. 8a and 8b illustrate another embodiment of a wearable device for sensing, displaying, and/or communicating a plurality of data corresponding to a user, in accordance with the present disclosure.
Figure 8B:
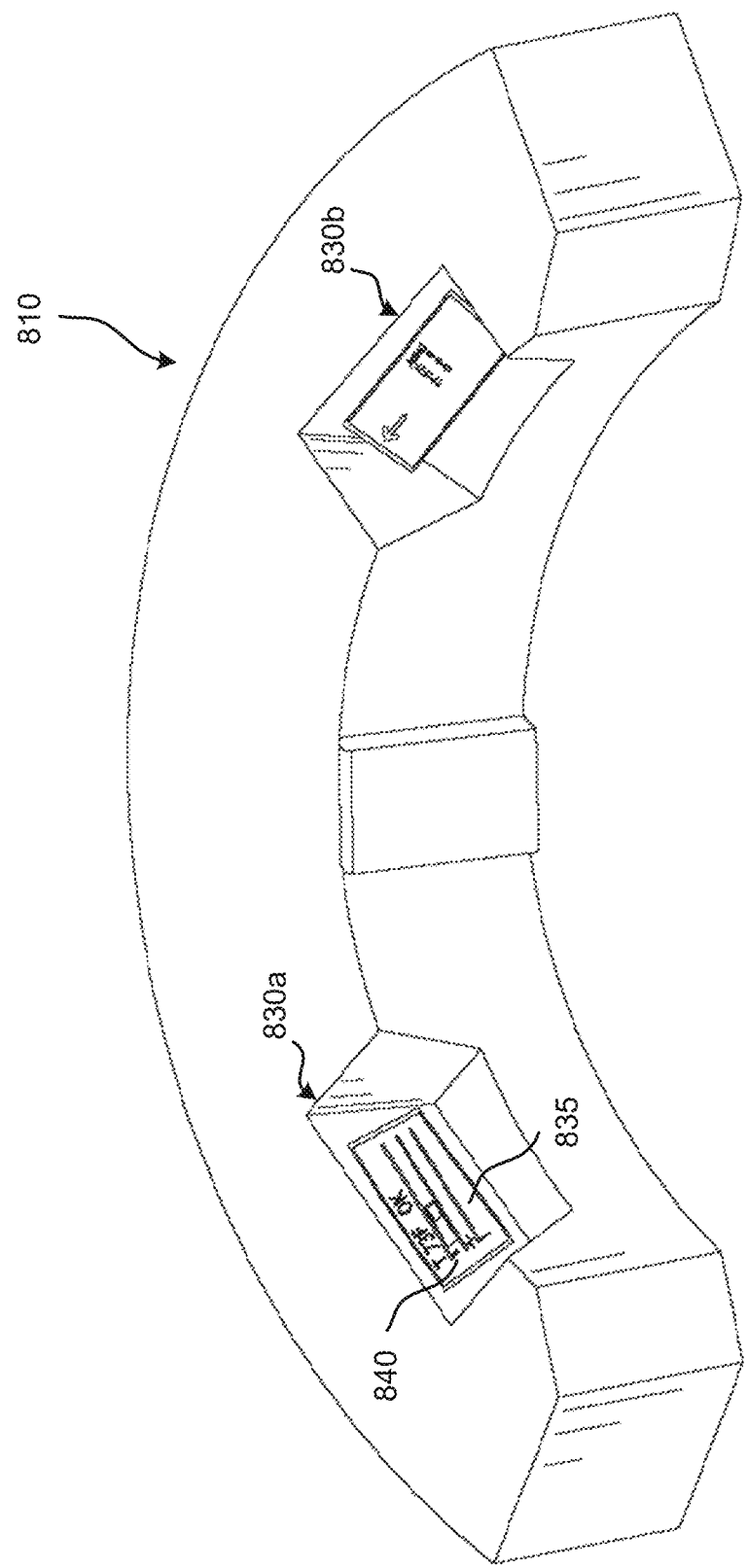

FIGS. 8a and 8b illustrate another embodiment of a wearable device 800, in accordance with the present disclosure, worn concurrently with headwear 820. The wearable device 800 can comprise a control unit 810, a biometric sensor unit (not shown, but similar to that illustrated in FIG. 4), and a display unit. The control unit 810 can comprise a dashboard 815 mounted to a front portion of the headwear 820. The dashboard 815 can comprise an arced, hollow enclosure that fits around a front portion of the headwear 820. The dashboard 815 can contain a plurality of devices and hardware, as discussed above, and also encase two display units 830a, 830b, as illustrated in FIG. 8b. The control unit 810 can be integrally connected to headwear 820 worn by a user and thereby comprise an attachment interface, as discussed above with respect to FIG. 2c. The attachment interface can comprise a fastener, such as a screw, that can screw into a corresponding socket thereby attaching the housing to the headwear. In contrast to the attachment interface illustrated in FIG. 2c, the attachment interface can include a fastener and socket on each side of the headwear. In other embodiments, the control unit 810 can be attached to the front of a mask of the headwear using adhesive or other suitable attachment mechanism.

As illustrated at FIG. 8b, the wearable device can include dual display units 830a, 830b embedded within the housing. The dual display units 830a, 830b can comprise screens on which a plurality of items of information can be displayed. Additionally, in some embodiments, each display unit 830a, 830b can display different information. For instance, display unit 830a can display the user's temperature, heart rate, action items, and battery life of the wearable device, while display unit 830b can show the user's acceleration in the x-, y-, and z-directions.

Figure 9A:
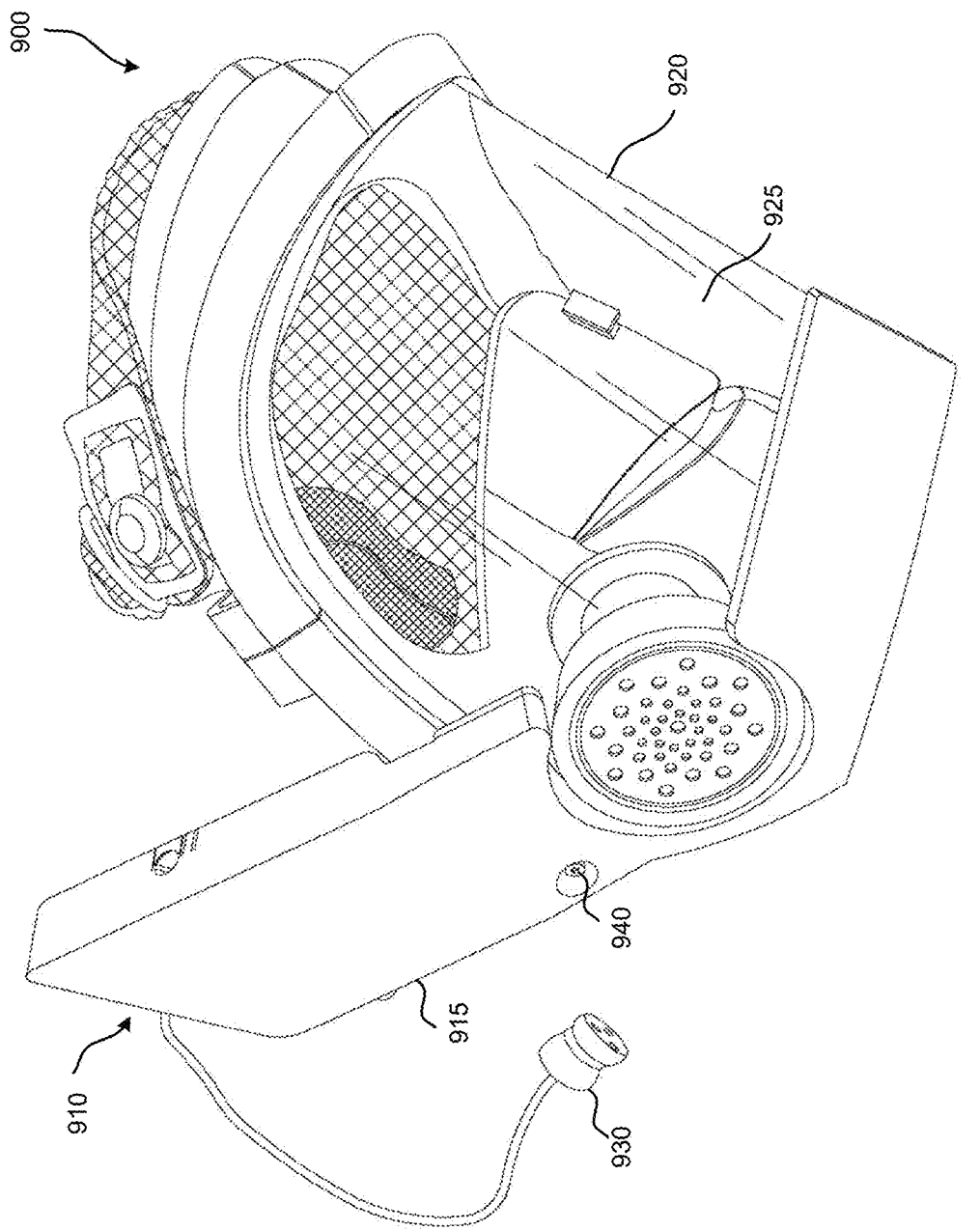
FIGS. 9a and 9b illustrate another embodiment of a wearable device for sensing, displaying, and/or communicating a plurality of data corresponding to a user, in accordance with the present disclosure.
Figure 9B:
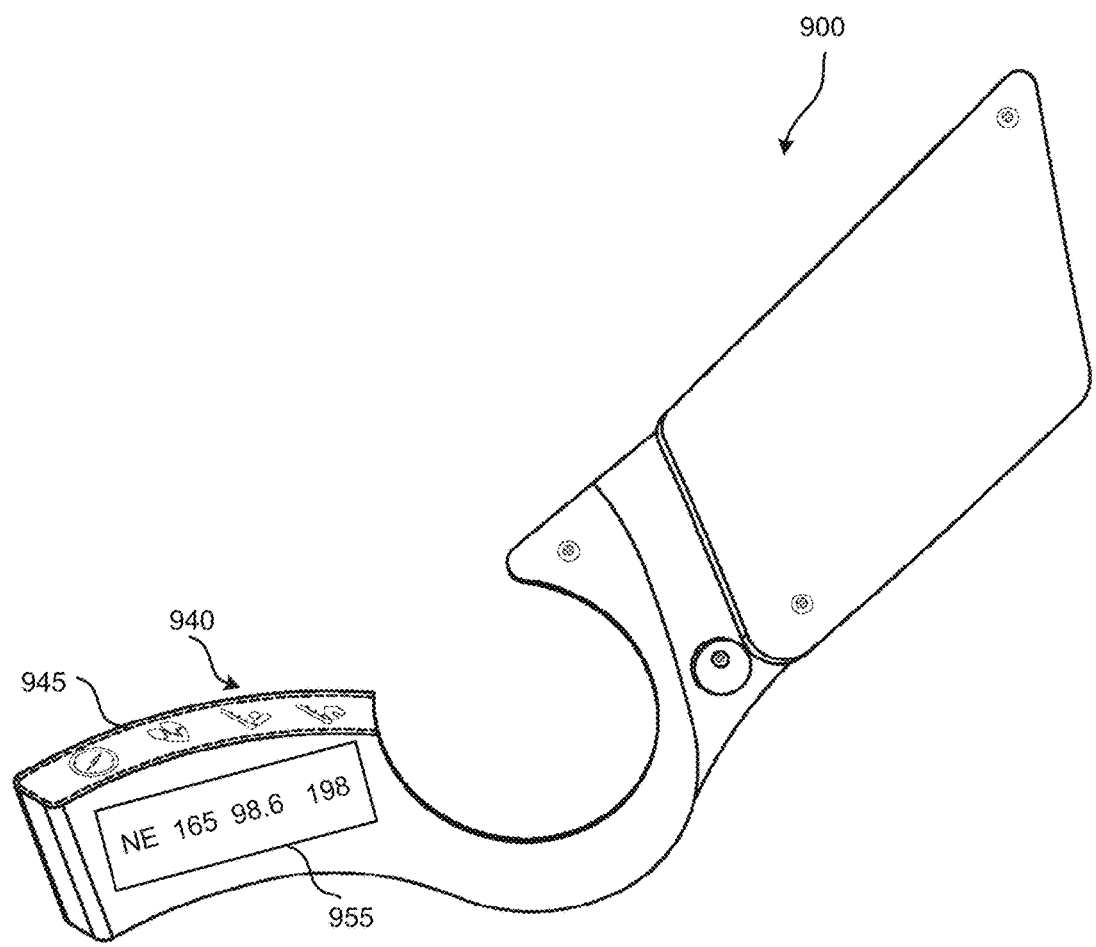

FIGS. 9a-9b illustrate another embodiment of a wearable device 900 in accordance with the present disclosure. As shown, the wearable device 900 comprises a control unit 910, a biometric sensor unit 930, and a display unit (illustrated in FIG. 9b). The control unit 910 can be attached to the headwear 920. As illustrated at FIG. 9a, the control unit 910 can comprise a housing 915 that is configured to wrap around a side of the headwear 920 and connect to an attachment interface. As shown in FIG. 9, the control unit 910 can comprise a housing 915 having an elongated portion that houses a plurality of hardware and devices. Additionally, a display unit 940 can be disposed external to the headwear 920 and can be located proximate a bottom portion of the visor 925.

As illustrated at FIG. 9b, the display unit 940 can comprise an icon portion 945 and a data portion 955. The icon portion 945 can be located on a top portion of the housing 915 of the control unit 910 and can comprise a plurality of icons indicative of individual biometrics. For instance, as illustrated at FIG. 9b, the plurality of icons can be a compass indicator, a heart rate indicator, an internal temperature indicator, and an external temperature indicator. The plurality of icons can be LED backlit and configured to change color (e.g. green, yellow, or red) to correspond to the range in which the user's biometric fall (discussed in more detail below). For instance, green can correspond to a biometric within a pre-determined range indicative of a normal level, yellow can correspond to a biometric exceeding the normal level and indicative of a warning that the biometric is approaching a risky level, and red where the biometric has reached a dangerous or unhealthy level. Such threshold ranges for color changes in the icons can be predetermined in accordance with similar methods as those discussed below with respect to FIGS. 11-12.

In some embodiments, the pre-determined range can be specific to the user. For instance, the pre-determined range can be calculated from a variety of metrics including the user's health characteristics, such as age, gender, weight, and height.

The data portion 955 can display alphanumeric representations of data associated with a user. For instance, as illustrated in FIG. 9b, the data portion can display the compass heading (e.g. NE), the heart rate (e.g. 165), the body temperature (e.g. 98.6) and the external temperature (e.g. 198). The data portion 955 can be configured to provide updated data corresponding to the data sensed by the biometric sensor unit. In other embodiments, the display unit 940 can include icons related to other biometrics and display data on the data portion 955 corresponding to various other biometrics, as described previously.

While the previously described embodiments are illustrated in reference to headwear, it is understood that the described wearable devices can be incorporated within a variety of garments, protective gear, or other objects. For instance, the control unit can attach to, or be incorporated into, the user's shirt, within the user's pocket, to the user's belt, or to SCBA or other protective helmets or masks.

Figure 10A:
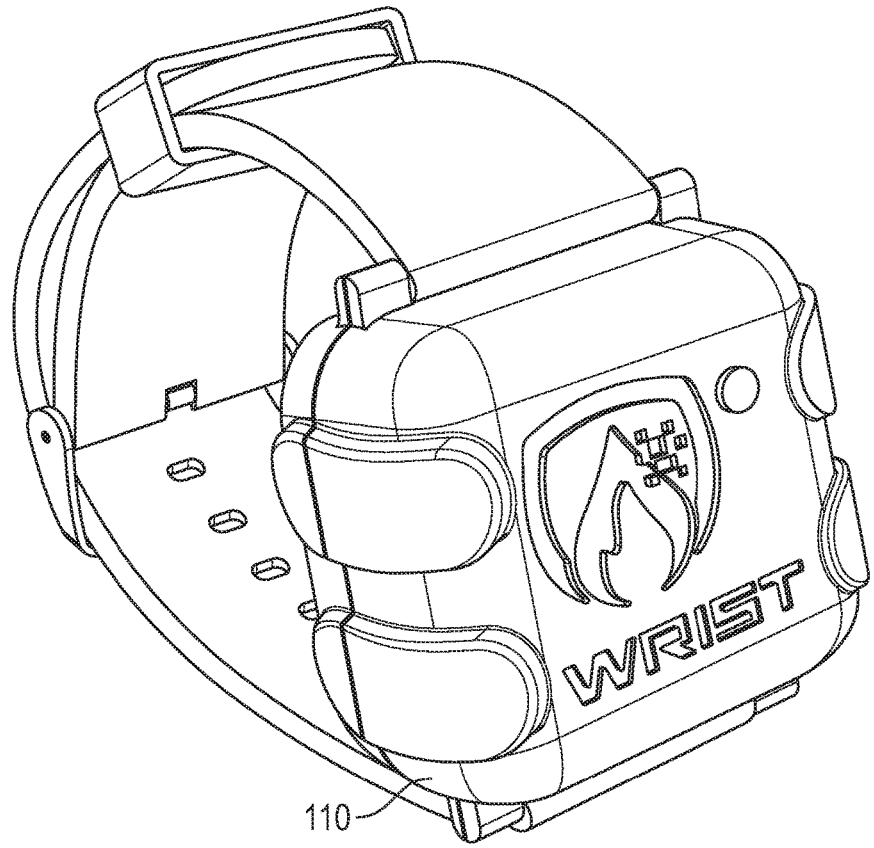
FIGS. 10a and 10b illustrate another embodiment a wearable device for sensing and/or communicating a plurality of data corresponding to a user, in accordance with the present disclosure.

Referring to FIG. 10a, the wearable device 110 can be integrated into a bracelet or forearm strap. In some embodiments, the wearable device 110 can be an anklet (i.e., a bracelet designed to be worn about the ankle), a sleeve (e.g., designed to be worn about the forearm, upper arm, thigh, or lower leg), a necklace, a ring, a vest, an adhesive patch, or any other wearable object. The wearable device can have some or all of the features discussed above with respect to the wearable devices depicted in, and/or discussed with respect to, FIGS. 1a-9b.

In some embodiments, the wearable device can comprise a control unit affixed to a strap, the strap for fastening around a wrist or forearm of the user. In some embodiments, the control unit can comprise a body and a face. The control unit can comprise some or all of the features discussed above with the control units depicted in, and/or discussed with respect to, FIGS. 1a-9b.

In some embodiments, the control unit can house a communication module configured to connect to a network. In some embodiments, the network connection device can be configured with a communication module can be configured to communicate using Bluetooth™ Bluetooth™ low-energy (BLE), WiFi™, ZigBee™, LoRaWAN protocol or other LoRa protocols, or using any other communication protocol, technology, or method. Those skilled in the art will understand that "LoRa" refers to a long-range connection.

Figure 10B:
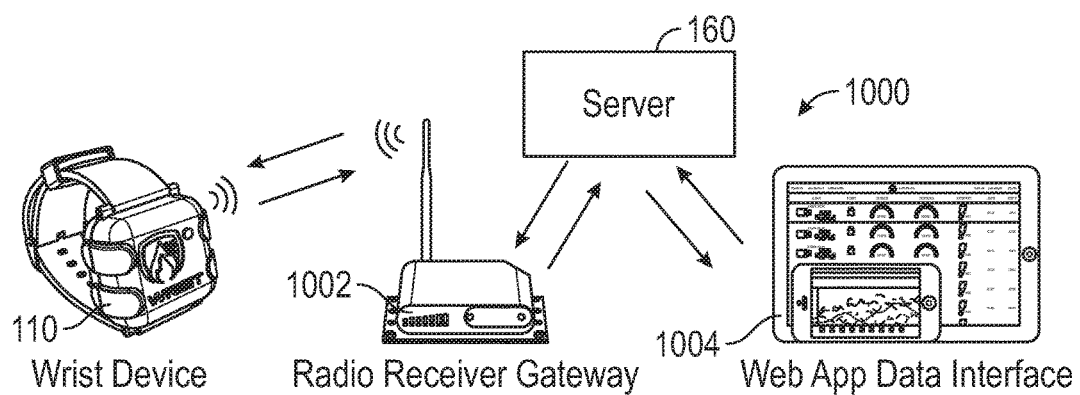

Referring to FIG. 10b, in some embodiments, the communication module can be configured to communicate with a gateway device 1002 using a first communication method when the wearable device 110 is within communication range of the gateway device 1002. When the wearable device 110 is outside of communication range of the gateway device 1002, the communication module may be configured to communicate with (e.g., transmit biometric data to) a nearby, predetermined communication device (e.g., a mobile phone, a computer) such that the communication device can relay the communication (e.g., transmit received biometric data) to, for example, a server 160. In some embodiments, the wearable device 110 may be configured to communicate with the nearby, predetermined communication device via Bluetooth™ Bluetooth™ low-energy (BLE), Near-Field Communication (NFC), or some other communication technology, protocol, or method. In some embodiments, the communication module of the wearable device 110 may be configured to transmit data via a second method when the wearable device 110 is outside the communication range of the gateway device 1002. In some embodiments, the wearable device 110 may be configured to transmit data via the second method to the gateway device 1002. In some embodiments, the wearable device 110 may be configured to transmit data via the second method to a device that is different from the gateway device 1002. For example, in some embodiments, the communication module may have 3G, 4G, 4G LTE, or 5G capabilities or may have a modem or other technology permitting the communication module to transmit data via a second method to the server 160 or other device via a different communication path and/or network.

In some embodiments, the wearable device 110 can comprise a user detection module (e.g., user detection module 680) that can detect when a user is wearing the wearable device. In some embodiments, the use detection module can use the accelerometer, gyroscope, and proximity sensor to detect when it is on a user or otherwise in use. In certain embodiments, the use detection module can include a biometric authentication device. The biometric authentication device can include a biometric sensor or scanner configured to detect identifying biometric information associated with a user, and the biometric authentication device can compare the detected identifying biometric information to saved identifying biometric information and determine, based on the comparison of the detected identifying biometric information to the saved identifying biometric information, an identity of the user. As described above, each wearable device 110 may have a unique identifier, and the wearable device 110 may be configured to associate the user's identity with the unique identifier. In some embodiments, the wearable device 110 may associate the user's identity with the unique identifier until the wearable device 110 is moved out of contact with the user, runs out of power, is turned off, or otherwise loses the ability to monitor biometric information associated with the user (e.g., biometric information indicative of the user's wellbeing or activity).

In some embodiments, the biometric authentication device may be configured to identify a user via one or more of a detected fingerprint, hand geometry, earlobe geometry, retina pattern, iris pattern, voice waves, or DNA (such as from detected sweat, saliva, skin). That is, in some embodiments, the wearable device 110 may include one or more biometric scanners, which may include but are not limited to a fingerprint scanner, an iris scanner, a retinal scanner, a camera, a microphone, a DNA tester, or any other device configured to identify a user via detected biometric information.

In some embodiments, the biometric authentication device may be configured to detect biometric information and transmit data the biometric information to the server 160, such as via gateway device 1002, and the server 160 may be configured transmit data to a viewing device 1004 such that data corresponding to or more wearable devices 110 can be viewed and/or monitored (e.g., via a web app data interface). The server 160 may be configured to determine, based on a comparison of the detected biometric information to the saved biometric information, an identity of the user. The server may then transmit the identity of the user to the wearable device 110 and/or may transmit instructions, to the wearable device 110, to begin transmitting biometric information indicative of the user's wellbeing or activity. In some embodiments, the server does not transmit instructions to the wearable device 110, and the wearable device 110 is instead configured to automatically begin transmitting detected biometric information indicative of the user's wellbeing or activity.

In some embodiments, the wearable device can be configured to communicate with the radio receiver gateway 1002 and/or server using direct connections such as radio-frequency identification (RFID), near-field communication (NFC), Bluetooth™, Bluetooth™ low-energy (BLE), WiFi™, ZigBee™, LoRaWAN protocol or other LoRa protocols, ambient backscatter communications (ABC) protocols, USB, or LAN.

In some embodiments, the control unit can comprise an online mode and an offline mode. As used herein, the "offline mode" (or otherwise referred to the wearable device being asleep) can refer to a state of the control unit in which the control unit is unable to, and not attempting to, connect to a network and/or gateway device such that information cannot be transmitted. As used herein, the "online mode" (or otherwise referred to the wearable device being awake) can refer to a state of the control unit in which the control unit is able to connect to a network and/or gateway device such that information can be transmitted. In some embodiments, the wearable device 110 can be configured to while asleep, periodically (e.g., every five, ten, fifteen, thirty, or sixty seconds) determine whether a user is wearing or otherwise using the wearable device 110. If the identity detection module does not determine that the wearable device 110 is being used, the wearable device can return to sleep. If the identity detection module does determine that wearable device 110 is being used, the wearable device can transition to online or awake mode and can identify a user and/or being transmitting detected biometric information.

According to some embodiments, the gateway device 1002 may be configured to receive data from one or more wearable devices 110 any may be configured to transmit some or all of the received data to web server (e.g., server 160) via a mobile network, such as by 3G, 4G, 4G LTE, or 5G capabilities. In this way, some or all of the data originally transmitted by the wearable device 110 can be accessed by a remote unit 120, as described herein.

In some embodiments, the gateway device 1002 may include a router or other device capable of broadcasting a local Wi-Fi network. In some embodiments, the gateway device 1002 may be configured to determine if the mobile network is not viable (e.g., connection strength or signal strength is too low, data is not being transmitted at a sufficient speed) or if the gateway device is otherwise unable to connect to the mobile network. Upon determining that the mobile network is not viable or that the gateway device 1002 cannot connect to the mobile network, the gateway device 1002 may be configured to broadcast a local Wi-Fi network, which may enable a user to connect to the gateway device 1002 via the local Wi-Fi network to access and/or view biometrics of one or more users. In some embodiments, the gateway device 1002 may have some or all of the instructions, code, and/or functionality of a web server (e.g., server 160) such that gateway device 1002 can serve the same functionality as a server. Thus, according to some embodiments, if the gateway device 1002 determines that a viable connection to the mobile network is not viable, the gateway device 1002 may be configured to initiate and maintain a local wireless network, such as via Wi-Fi technology, such that the remote unit 120 or some other device can connect to the local wireless network to view some or all data received from wearable devices 110.

In certain embodiments, the wearable device 110 can be configured to determine whether it is out of communication range with the gateway device 1002. Upon determining that the wearable device 110 is out of communication range with the gateway device 1002, the wearable device 110 may be configured to transmit data to, and/or receive data from, a separate, predetermined communication device (e.g., a mobile phone, a computer) such that the communication device can relay data to, for example, a server 160, as described herein. Thus, the server 160 can provide some or all of the data originally transmitted from the wearable device 110 such that the data can be viewed from the remote unit 120 or some other device configured to access data from the server 160 (e.g., via the Internet).

Further, in some embodiments, the wearable device 110 may be configured to store detected data upon determining that the wearable device 110 is out of communication range with the gateway device 1002 and is out of communication range with the separate, predetermined communication device. The wearable device 110 may be configured to continuously store detected data until communication is established with the gateway device 1002 or the predetermined communication device, and upon establishing communication with the gateway device 1002 or the predetermined communication device, the wearable device 110 may be configured to transmit some or all of the stored data to the gateway device 1002 or the predetermined communication device.

In some embodiments, the wearable device described above can also be in communication with a computer-executable application remotely located from the wearable device. The computer-executable application can be configured for receiving, displaying, and/or tracking the plurality of biometric data corresponding to a user of the remote device.

As described above, the control unit of the wearable device can comprise a communication unit, including a transmitter and a receiver, for transmitting the biometric data to the application and receiving a plurality of messages from the application. The remote unit can include a separate communication unit (as illustrated at FIGS. 1a and 1b). The application can be implemented on any platform including, but not limited to, a desktop or lap-top computer, a tablet computer, a mobile phone, or other computing device. FIGS. 1a and 1b, discussed previously, illustrate an exemplary remote unit 120 for allowing communication from the wearable device 110 to a remote user accessing the remote unit. The remote unit 120 can comprise, for instance, a command station, a base station, a wearable device user accessing a profile tracking his individual metrics. Or, in some embodiments, the remote unit 120 can be a server or other intermediary device.

Figure 11:
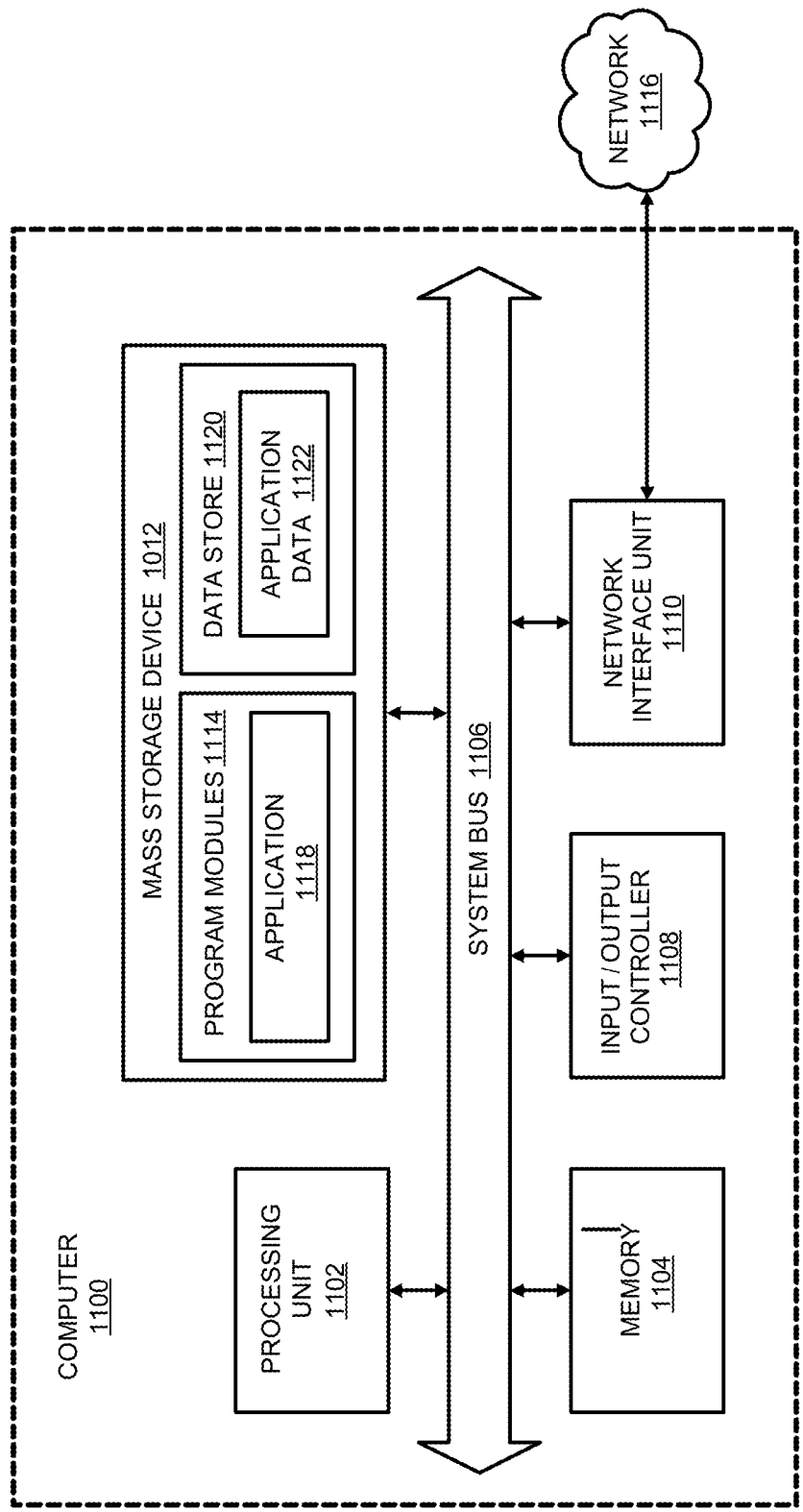
FIG. 11 is an exemplary computer architecture for use with various aspects of a computer-executable application, in accordance with an embodiment of the present disclosure.

FIG. 11 is a computer architecture diagram showing a general computing system capable of implementing aspects of the disclosed technology in accordance with one or more embodiments described herein. A computer 1100 may be configured to perform one or more functions associated with, for example, the remote unit 120 shown in FIGS. 1a and 1b and aspects of the computer-executable application illustrated with respect to FIGS. 12-14. For example, the computer 1100 may be configured to perform various aspects of receiving, processing, displaying, and/or transmitting a plurality of biometric data received from and/or transmitted to a wearable device to a remote user accessing an application. It should be appreciated that the computer 1100 may be implemented within a single computing device or a computing system formed with multiple connected computing devices. The computer 1100 may be configured to perform various distributed computing tasks, in which processing and/or storage resources may be distributed among the multiple devices.

As shown, the computer 1100 includes a processing unit 1102 ("CPU"), a system memory 1104, and a system bus 1106 that couples the memory 1104 to the CPU 1102. The computer 1100 further includes a mass storage device 1112 for storing program modules 1114. The program modules 1114 may be operable to perform various functions associated with associated with receiving, processing, and displaying a plurality of biometric data received from a wearable device to user accessing an application, as illustrated in one or more of FIGS. 12-14 discussed above. The program modules 1114 may include a computer-executable application 1118 for performing data acquisition and/or processing functions as described herein, for example to acquiring, calculating, organizing, and analyzing data associated with a condition of the user. The computer 1100 can include a data store 1120 for storing data that may include biometric-related data 1122 such as indications of sensed biometric data corresponding to a physiological condition of a user, in accordance with various embodiments.

The mass storage device 1112 is connected to the CPU 1102 through a mass storage controller (not shown) connected to the bus 1106. The mass storage device 1112 and its associated computer-storage media provide non-volatile storage for the computer 1100. Although the description of computer-storage media contained herein refers to a mass storage device, such as a hard disk or CD-ROM drive, it should be appreciated by those skilled in the art that computer-storage media can be any available computer storage media that can be accessed by the computer 1100.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 1100. "Computer storage media", "computer-readable storage medium" or "computer-readable storage media" as described herein do not include transitory signals.

According to various embodiments, the computer 1100 may operate in a networked environment using connections to other local or remote computers through a network 1116 via a network interface unit 1111 connected to the bus 1106. The network interface unit 1110 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems. The computer 1100 may also include an input/output controller 1108 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 1100. The bus 1106 may enable the processing unit 1102 to read code and/or data to/from the mass storage device 1112 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology.

The computer storage media may also represent secondary storage, whether implemented as hard drives or otherwise. Hard drive implementations may be characterized as solid state or may include rotating media storing magnetically-encoded information. The program modules 1114, which include the imaging application 1118, may include instructions that, when loaded into the processing unit 1102 and executed, cause the computer 1100 to provide functions associated with one or more example embodiments and implementations illustrated in, for example, FIGS. 1a, 1b, and 12-14. The program modules 1114 may also provide various tools or techniques by which the computer 1100 may participate within the overall systems or operating environments using the components, flows, and data structures discussed throughout this description.

In general, the program modules 1114 may, when loaded into the processing unit 1102 and executed, transform the processing unit 1102 and the overall computer 1100 from a general-purpose computing system into a special-purpose computing system. The processing unit 1102 may be constructed from any number of transistors or other discrete circuit elements, which may individually or collectively assume any number of states. More specifically, the processing unit 1102 may operate as a finite-state machine, in response to executable instructions contained within the program modules 1114. These computer-executable instructions may transform the processing unit 1102 by specifying how the processing unit 1102 transitions between states, thereby transforming the transistors or other discrete hardware elements constituting the processing unit 1102. In other embodiments the processing unit can operate as a real time operating system configured to schedule and coordinate multiple tasks from the sensors, communication units, etc.

Encoding the program modules 1114 may also transform the physical structure of the computer-storage media. The specific transformation of physical structure may depend on various factors, in different implementations of this description. Examples of such factors may include, but are not limited to, the technology used to implement the computer-storage media, whether the computer storage media are characterized as primary or secondary storage, and the like. For example, if the computer storage media are implemented as semiconductor-based memory, the program modules 1114 may transform the physical state of the semiconductor memory, when the software is encoded therein. For example, the program modules 1114 may transform the state of transistors, capacitors, or other discrete circuit elements constituting the semiconductor memory.

As another example, the computer storage media may be implemented using magnetic or optical technology. In such implementations, the program modules 1114 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

In some embodiments, the computer-executable application associated with the remote unit may be accessible by a variety of users simultaneously. The computer-executable application can receive a plurality of biometric data from one or more users of the wearable device. The received biometric data can include a variety of biometric data including, but not limited to, ambient temperature, body temperature, heart rate, oxygen consumption, oxygen saturation of the blood, blood pressure, energy expenditure, respiration rate, speed, calories burnt, steps taken, cardiac efficiency, and heart rate variability. A remote user using the computer-executable application can then track the biometric data received from the wearable device. Additionally, in some embodiments, the computer-executable application can permit the remote user to transmit a plurality of messages to users wearing the wearable device. For instance, the remote user can transmit messages regarding biometrics of the user wearing the wearable device, such as telling such user to take a break, or action items for the user to perform. In other embodiments the remote user can transmit a plurality of messages to multiple users wearing wearable devices, at the same time. In some embodiments, the computer-executable application can be configured to extract a numerical representation of the sensed biometric data from indications of the biometric data transmitted from the wearable device. The computer-executable application can then analyze the biometric data to provide a method for a remote user to monitor biometric data associated with a user of the wearable device. For instance, the computer-executable application may be configured to compare the numerical representation of the sensed biometric data to a threshold value corresponding to a predetermined biometric range and create one or more graphical representations of the sensed biometric data for display on the graphical user interface. The one or more graphical representations will be discussed in further detail with respect to FIGS. 12-14.

Following display of the graphical representations to the remote user, the remote user may generate one or more messages to communicate with a user of the wearable device. For instance, the computer-executable application can generate one or more messages indicating at least one of i) the biometric data associated with the user of the wearable device, ii) action items to be performed by the user of the wearable device, and iii) status messages associated with a condition of the user of the wearable device.

Figure 12:
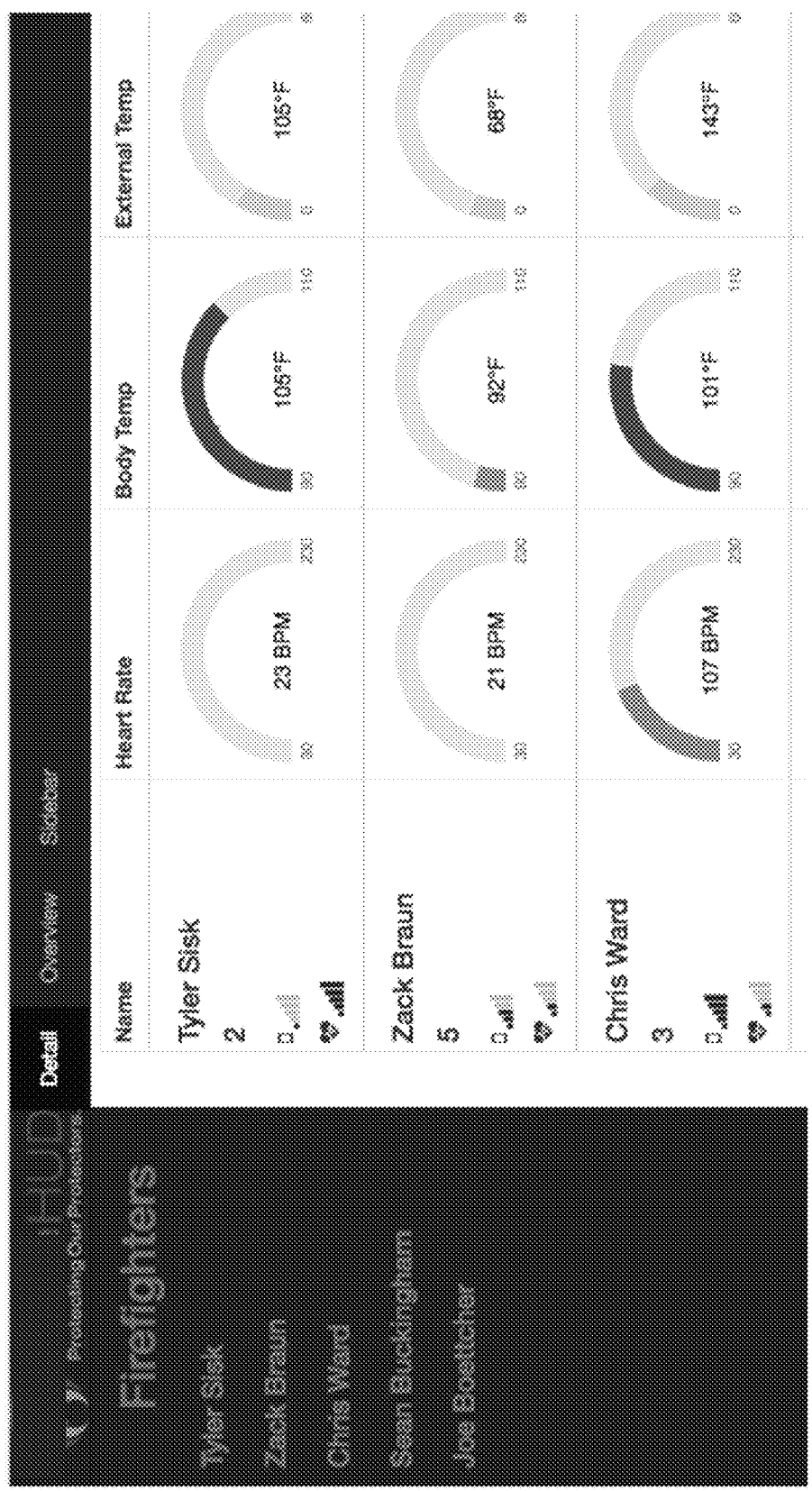
FIG. 12 illustrates a graphical user interface of a computer-executable application, in accordance with an embodiment of the present disclosure.
Figure 13:
FIG. 13 is another illustration of a graphical user interface of a computer-executable application, in accordance with an embodiment of the present disclosure.

The computer-executable application associated with the remote unit can comprise a graphical user interface (GUI). FIGS. 12-14 illustrate a variety of examples of GUIs that can be visible to a user when accessing the application. The GUIs can comprise a variety of windows, icons, and menus through which a user can interact with the application. For example, as illustrated at FIGS. 12-13, the GUI can comprise a window displaying a table comprising a plurality of charts associated with different biometrics. The plurality of charts can comprise any variety of charts that can display different biometrics, for instance histograms, gauge charts, and line charts. For instance, FIGS. 12-13 illustrate a plurality of gauge charts indicative of heart rate, body temperature, external temperature, and VO2$_{max}$ within a particular range. The gauge charts can comprise a variety of colors in a spectrum indicative of where the detected biometric falls in a range from normal or safe to abnormal or unsafe. For instance, as illustrated at FIGS. 12-13, the gauge for heart rate can display a range of BPMs between 30 and 230 BPM. In some embodiments, the GUI can display the heart rate of the user of the wearable device underneath the gauge chart and the gauge chart can change colors. For instance, green can correspond to a heart rate in a normal range, yellow can correspond to a heart rate in a moderately unhealthy or dangerous range, and red can correspond to a heart rate in a highly unhealthy or dangerous range. Exemplary ranges that these biometrics fall in are illustrated in Table 1. Similar concepts can be applied to body temperature, external temperature, and VO2$_{max}$ measurements received, as well as any other biometric of interest.

Additionally, other metrics can be included in the chart, including the number of calories burned by a user, the number of steps taken, the battery life of the wearable device, and the respective wireless connections between the wearable device and the remote device accessing the application. Other metrics that can be displayed in the chart further include a level of fatigue, respiration rate, speed, cardiac efficiency, and heart rate variability. Table 1 below illustrates the ranges in which a user will receive different updates including whether certain biometrics are within a safe, warning, or danger range, and what measurements fall into what range. The ranges for each of the biometrics, such as those shown in Table 1, can be measured by the wearable device and can be predetermined in the application. Additionally, the thresholds set for charts, such as gauge charts, that illustrate biometric levels with incident color changes can be set via the application.

FIG. 14 illustrates another exemplary GUI in accordance with another embodiment of the present disclosure. The GUI illustrated in FIG. 14 is an abbreviated version of that shown in FIG. 14. The GUI can display various fields including "unit #," "name," "status," and a message for each respective user. The "unit #" field can correspond with the number of the wearable device worn by the user. The "status" field can display any bodily status that may be outside a normal range, such has "High HR" corresponding to a high heart rate. Additionally, the message field can display a particular message conveyed to a user in response to the status of that user's biometrics. Additionally, the application can display various "action items" that need to be carried out by the users.

Additionally, in some embodiments, the computer-executable application can include the ability to predict fatigue using machine learning. For instance, the application can comprise a variety of machine learning techniques including, but not limited to, Multi-class classification, two-class classification, regression and anomaly detection. Additionally, the machine learning algorithm can include any of Naïve Bayes Classification, Ordinary Least Squares Regression, Logistic Regression, Support Vector Machine, Ensemble methods, Principal Component Analysis, Gaussian Naïve Bayes, Multinominal Naïve Bayes, Bayesian Belief Networks, K-means, Neural Networks, etc. In some embodiments, using machine learning algorithms, discrete classification of fatigue levels can be obtained based off of both current and historical biometric data to predict fatigue of users in real time. Such learning can be achieved, for instance, in the context of supervised, reinforced or unsupervised learning by the algorithm and could also include deep learning (having multiple layers made up of the above machine learning algorithms such as first using a Support Vector Machine followed by using Logistic Regression).

TABLE 1

| Data Item | Minimum Value | Maximum Value | Safe Range | Warning Range | Danger Range | Units |
|---|---|---|---|---|---|---|
| External Temperature | 0 | 1000 | 0-400 | 400-700 | 700-1000 | Degrees Fahrenheit |
| Internal Temperature | 0 | 110 | 96-100 | None | 0-96 & 100-110 | Degrees Fahrenheit |
| Heart Rate | 0 | 200 | 45-120 | 120-160 | 0-45 & 160-200 | Beats/min |
| Battery | 0 | 100 | 50-100 | 30-50 | 0-30 | Percentage |
| VO$_{2max}$ | 0 | 100 | 38-100 | 28-37 | 0-27 | ml/kg/min |
| Heart Rate Quality Signal | 0 | 100 | 50-100 | 30-50 | 0-30 | Percentage |
| Steps | 0 | N/A | N/A | N/A | N/A | Number of Steps |
| GSM Quality Signal | 0 | 100 | 50-100 | 30-50 | 0-30 | Percentage |

Additionally, the ranges and thresholds chosen for monitoring various biometrics can be tuned to individual users. For instance, ranges can be determined based on the height, weight, age, and/or gender of the user. Additionally, ranges can be determined to compensate for activities engaged in by the user. For example, a nominal heart rate of the user may be computed to compensate for physical activity, such as carrying heavy loads, running, walking up stairs, in addition to bodily responses to emergency or exciting situations such as perpetuated adrenaline release, which can result in increases in the rate of blood circulation and breathing.

In some embodiments, cloud-based software may be configured to monitor incoming biometrics and categorize the incoming biometrics in real time (i.e., as instantaneous as possible) or near real time (i.e., with a delay in the range of 0.1 second to 5 seconds). In some embodiments, a maximum effort heart rate or threshold for a dangerous level of heart rate is calculated by subtracting a user's age in years from the number 220. In some embodiments, any heart rate values over 100% of a user's maximum effort heart rate is included in a dangerous level heart rate range. In some embodiments, 70% of a user's maximum effort heart rate is defined as the user's working level heart rate. In some embodiments, a user's working level heart rate range includes heart rate values that are between 70% and 100% of the user's maximum effort heart rate. In some embodiments, a user's working level heart rate range includes heart rate values that are between 70% and 84% of the user's maximum effort heart rate, and heart rate values over 84% of the user's maximum effort heart rate is included in a dangerous level heart rate range. In some embodiments, a safe range of heart rate values includes heart rate values that are between 50% and 70% of the user's maximum effort heart rate. In some embodiments, a resting range of heart rate values includes any heart rate values below 50% of the user's maximum effort heart rate. Aggregation of a user's heart rate values in the resting range can be used to calculate the user's average resting heart and average core body temperature while at rest.

To calculate a user's core body temperature, a running calculation can be computed based on the user's heart rate data over the previous 30 minutes, the user's average resting heart rate, the user's current heart rate, and the user's last known core body temperature while at rest. To calculate a Physiological Strain Index (PSI), which quantifies a user's exertion on a scale of 1-10, a calculation can be computed based on the user's current core body temperature, current heart rate, average resting core temperature, and average resting heart rate.

Figure 15:
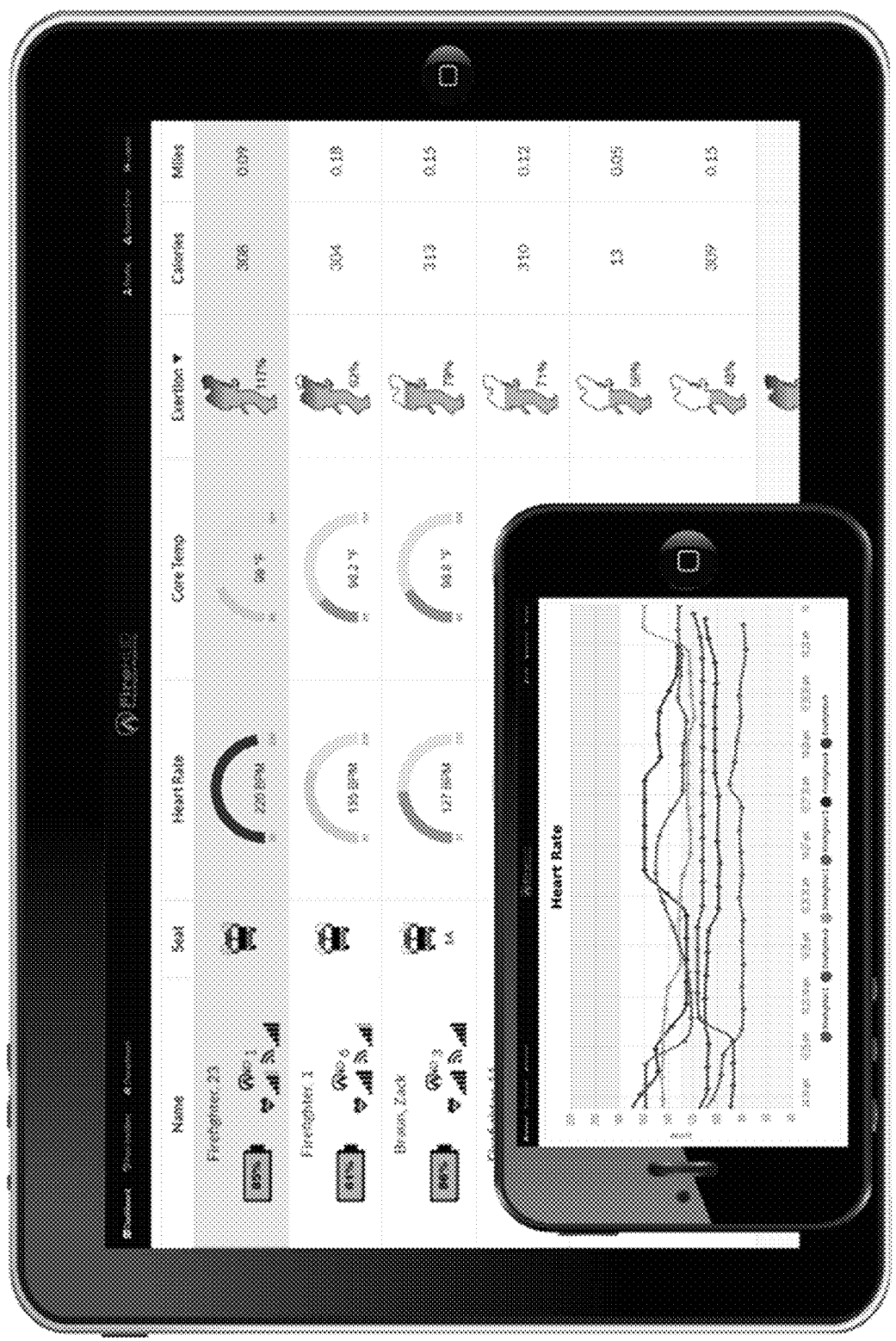
FIG. 15 illustrates a graphical user interface of a computer-executable application, in accordance with an embodiment of the present disclosure.

In some embodiments, personal information, such as a user's age or various heart rate values or ranges (e.g., dangerous, working, safe, resting) may be calculated but not viewable. That is, in some embodiments, only a percentage of a user's maximum effort heart rate and/or heart rate range (e.g., dangerous, working, safe, resting) can be displayed or otherwise viewable. For example, as shown in FIG. 15, various biometric data corresponding to multiple users can be displayed according to percentages of a maximum value. That is, some data type (e.g., a particular user's exertion) can be displayed according to a percentage of a maximum value of the corresponding data type. Some data types, such as current heart rate, current core body temperature, calories burned, and distance traveled may be displayed as numerical values. Stated otherwise, in some embodiments, data associated with one or more users may be anonymized and may be viewable alone or in aggregation with data associated with one or more additional users. Thus, in some embodiments, data for a particular individual, group, or demographic may be displayed anonymously. Further, in some embodiments, data may be displayed by city, county, region, state, country, or by any other grouping. In some embodiments, historical data associated with one or more users can be displayed by user or anonymously and/or by a particular grouping (e.g., by fire station, by city, by demographic). This may be useful in determining trends associated with an individual user or with a group of users.

Figure 16A:
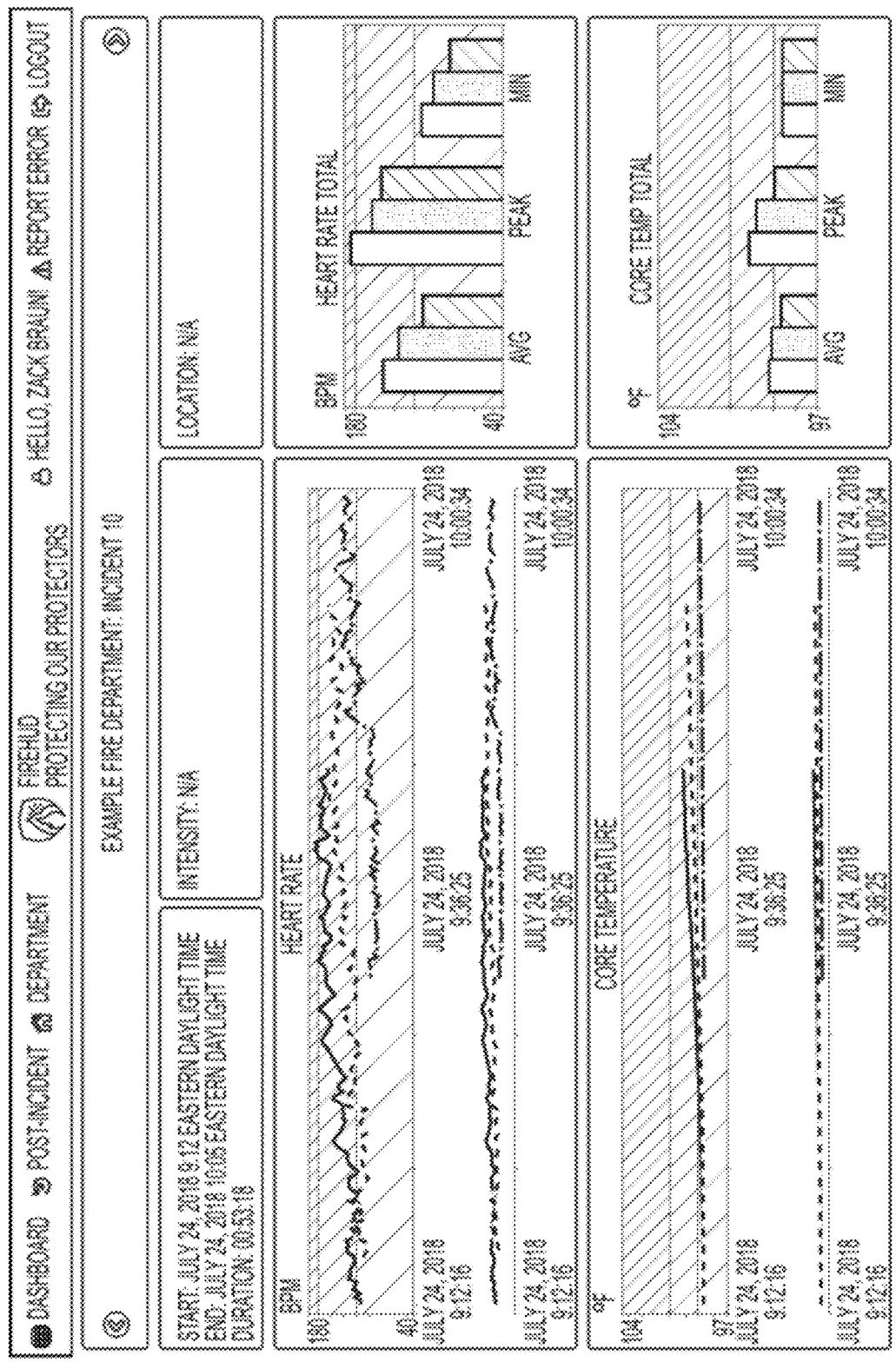
FIGS. 16a and 16b illustrate a graphical user interface of a computer-executable application, with the graphical user interface being split for clarity into an upper portion and a lower portion shown in FIGS. 16a and 16b, respectively, in accordance with an embodiment of the present disclosure.
Figure 16B:
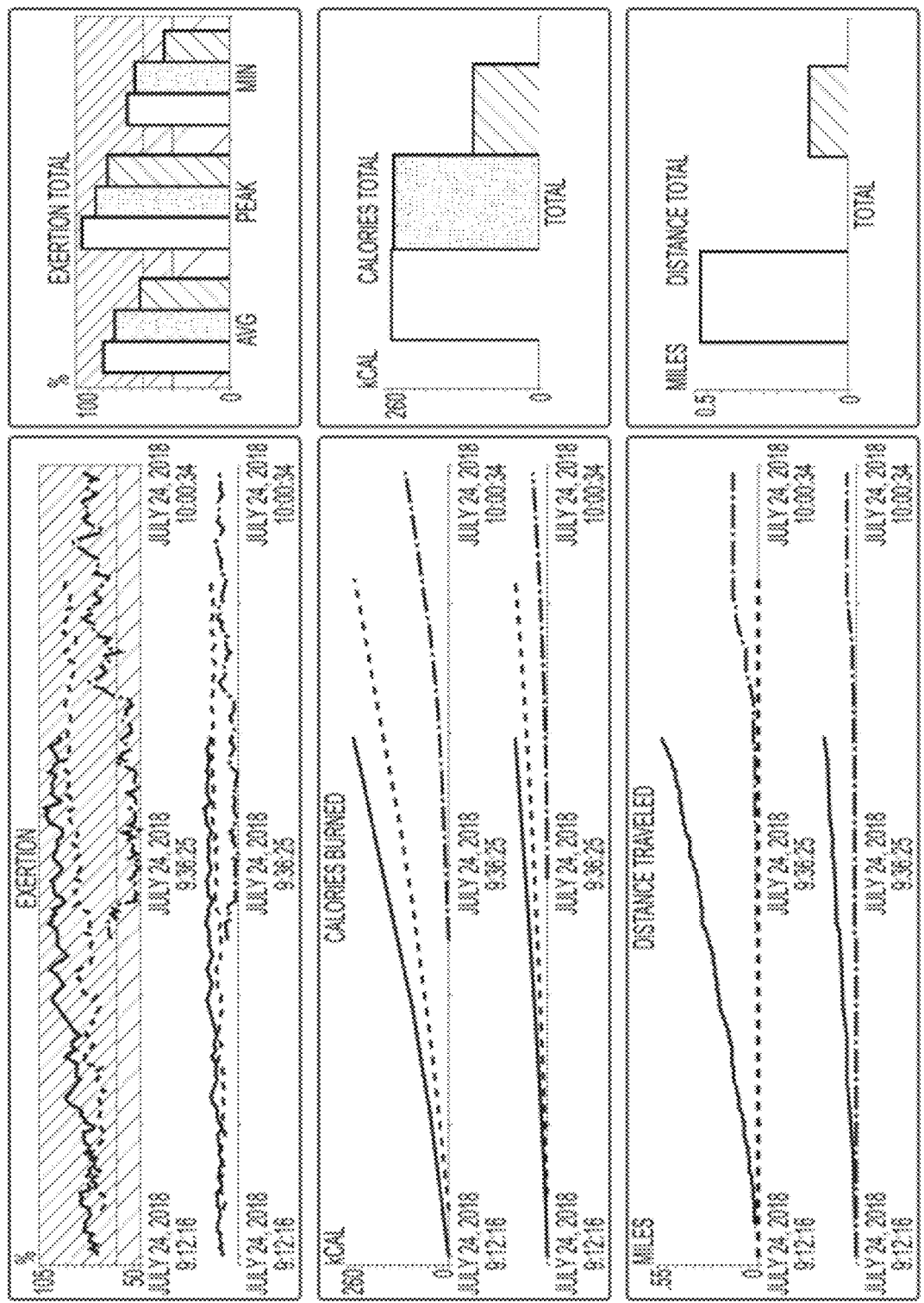

According to some embodiments, an event can be identified by determining when the heart rate of one or more users rises above a predetermined threshold. In some embodiments, the predetermined threshold is the respective resting heart rate threshold (i.e., 50% of maximum effort heart rate) for each user. In some embodiments, a post-incident analysis may be provided in which incidents and/or users can be compared directly or can be compared by group or demographic, such as by age, years of experience, or incident intensity. In some embodiments, incident intensity may be an inputted value that can be determined based on a post-incident evaluation of an incident. In some embodiments, the incident intensity may be based, at least in part, on biometric information received from one or more wearable device devices 110 and associated with a single incident. In some embodiments, the incident intensity may be indicative of a severity of an incident (e.g., scope or amount or cost of damage caused, heat values associated with a fire), a location of an incident, amount or number of injuries caused by an incident, or other factors that can describe the intensity or severity of an incident. In certain embodiments, the incident intensity can be a value on a scale (e.g., a scale of one to five) or can be indicative of an intensity grouping (e.g., one of a low intensity, medium intensity, or high intensity). The incident intensity may permit an organization to identify areas that can be improved. For example, an organization may realize that all users with fewer than two years of experience do not handle a particular situation as well as their more experience colleagues, and the organization may determine that additional training is required for the junior group of users. In certain embodiments, incidents may be grouped by severity and biometric data for each user can be averaged by group to create a baseline measure for different types of incident. These incident-specific baseline measures can be used to determine when a user's real-time biometric data is outside a normal range of values for that particular type of incident, and if so, an alert can be transmitted to an official or an authorized user. For example, as shown in FIGS. 16a and 16b, various biometric data corresponding to multiple users (e.g., three users, as depicted in FIGS. 16a and 16b) can be tracked across a particular event and can be displayed simultaneously via a web app interface or some other display.

The various embodiments described above are provided by way of illustration only and should not be construed to limit the scope of the present disclosure. Those skilled in the art will readily recognize various modifications and changes that may be made to the present disclosure without following the example embodiments and applications illustrated and described herein, and without departing from the true spirit and scope of the disclosure as set forth in the appended claims.

What is claimed is:

1. A wearable device for sensing and communicating data associated with a condition of a user, the wearable device comprising:
   a biometric sensor unit configured to sense biometric data associated with a physiological condition of the user; and
   a control unit operatively coupled to the biometric sensor unit and a display unit, the control unit comprising:
   at least one processor configured to receive indications of the sensed biometric data and cause the display unit to display at least one visual representation of the biometric data to the user, and
   at least one communication unit, the communication unit configured to:
   determine whether the wearable device is within a communication range of a remote unit,
   responsive to determining that the wearable device is within the communication range of the remote unit, perform at least one of transmitting and receiving information associated with the sensed biometric data to and from the remote unit, respectively, and
   responsive to determining that the wearable device is not within the communication range of the remote unit, perform at least one of transmitting and receiving information associated with the sensed biometric data to and from a predetermined mobile device, respectively.

2. The wearable device of claim 1, wherein the biometric sensor unit comprises one or more sensors configured to sense a plurality of biometrics associated with the physiological condition of the user while using the wearable device, the plurality of biometrics comprising at least one of the user's body temperature, heart rate, $VO2_{max}$, respiration, steps taken, blood pressure, heart rate variability, and calories burnt.

3. The wearable device of claim 2, wherein the biometric sensor unit comprises an earpiece configured to at least partially insert into an ear of the user of the wearable device.

4. The wearable device of claim 1, wherein the display unit comprises at least one of a near-eye display and a heads-up display.

5. The wearable device of claim 1, wherein the display unit is configured to display the at least one visual representation to the user of the wearable device in a location of the wearable device that is clear from obstructing a main view of the user of the wearable device.

6. The wearable device of claim 1, wherein the communication unit of the control unit comprises at least one of a transmitter configured to transmit the biometric data to the remote unit and a receiver configured to receive information from the remote unit, the received information including one or more messages indicating at least one of i) the biometric data associated with the user of the wearable device, ii) action items to be performed by the user of the wearable device, and iii) status messages associated with a condition of the user of the wearable device.

7. The wearable device of claim 6, wherein the condition of the user of the wearable device comprises the physiological condition of the user of the wearable device while the wearable device is in use.

8. The wearable device of claim 1, wherein at least one of the biometric sensor unit, display unit, and control unit is selectively attachable to headwear of the user of the wearable device.

9. The wearable device of claim 1, wherein at least one of the biometric sensor unit and the control unit comprise one or more sensors configured to sense at least one of an internal or external temperature associated with the wearable device while the wearable device is in use.

10. A system for detecting and communicating data associated with a condition of a user of a wearable device, the system comprising:
a wearable device comprising:
a biometric sensor unit configured to detect biometric data associated with the condition of the user;
an identity detection module configured to automatically identify the user from among a plurality of users by:
receiving, from the biometric sensor unit, detected identifying biometric information;
comparing the detected identifying biometric information to saved identifying biometric information; and
determining, based on the comparison of the detected identifying biometric information to the saved identifying biometric information,
an identity of the user; and
a control unit operatively coupled to the identity detection module and the biometric sensor unit, the control unit configured to receive indications of the detected biometric data from the biometric sensor unit.

11. The system of claim 10, further comprising a remote unit in communication with the wearable device, the remote unit comprising:
one or more processors;
a memory;
a receiver configured to receive the indications of the detected biometric data from the control unit; and
a computer-executable application comprising a graphical user interface for interacting with a user of the remote unit, the computer-executable application being stored in the memory.

12. The system of claim 11, wherein the computer-executable application is executable by the one or more processors to perform functions that comprise at least one of:
extracting a numerical representation of the detected biometric data;
comparing the numerical representation of the detected biometric data to a threshold value corresponding to a predetermined biometric range;
creating one or more graphical representations of the detected biometric data for display on the graphical user interface; and
generating one or more messages indicating at least one of i) the biometric data associated with the user of the wearable device, ii) action items to be performed by the user of the wearable device, and iii) status messages associated with a condition of the user of the wearable device.

13. The system of claim 12, wherein wearable device is a wearable device of a plurality of wearable devices and the computer-executable application is executable by the one or more processors to perform additional functions that comprise at least one of:
creating, for display on the graphical user interface, one or more cumulative graphical representations of detected biometric data received from each wearable device of the plurality of wearable devices; and
creating, for display on the graphical user interface, one or more historical graphical representations indicating a time-based trend of detected biometric data received from at least one wearable device of the plurality of wearable devices.

14. The system of claim 10, wherein the identity detection module comprises at least one of an accelerometer, a gyroscope, and a proximity sensory, and wherein automatically identifying the user of the plurality of users comprises determining, based on data received the accelerometer, gyroscope, or proximity sensory, that the wearable device is being used.

15. The system of claim 10, wherein the biometric sensor unit comprises at least one sensor configured to sense a plurality of biometrics associated with a physiological condition of the user while using the wearable device, the plurality of biometrics comprising at least one of the user's body temperature, heart rate, $VO2_{max}$, respiration, steps taken, blood pressure, and calories burnt.

16. The system of claim 10, wherein the detected identifying biometric information comprises at least one of fingerprint data, hand geometry data, earlobe geometry data, retinal data, iris data, voice biometric data, and DNA data.

17. A method for detecting and communicating data associated with a condition of a user of a wearable biometric device, the method comprising:
receiving, from the wearable biometric device and at a gateway device, biometric data associated with a physiological condition of the user, the biometric data being detected by a biometric sensor unit of the wearable biometric device;

determining, by the gateway device, whether a communication module of the gateway device can establish or maintain a viable connection to a mobile network; and responsive to determining that the communication module cannot establish or maintain a viable connection to the mobile network, broadcasting, by a router module of the gateway device, a wireless local network such that a command communication device can access, via the gateway device, data detected by the wearable biometric device.

18. The method of claim 17, further comprising:

transmitting, by the gateway device and to a control unit, one or more messages including information associated with the biometric data.

19. The method of claim 17, further comprising transmitting, by the communication module and to a server, at least some of the biometric data such that the at least some of the biometric data can be accessed by a remote computing device and displayed by a graphical user interface of the remote computing device.

20. The method of claim 17, wherein the biometric data comprises at least one of the user's body temperature, heart rate, $VO2_{max}$, respiration, steps taken, blood pressure, and calories burnt while using the wearable biometric device.

* * * * *